US009096014B2

(12) United States Patent
Kumar et al.

(10) Patent No.: US 9,096,014 B2
(45) Date of Patent: Aug. 4, 2015

(54) ORIENTED POLYMERIC SHEETS EXHIBITING DICHROISM AND ARTICLES CONTAINING THE SAME

(75) Inventors: Anil Kumar, Murrysville, PA (US); Peter C. Foller, Murrysville, PA (US); David Park, Tuam (IE); Declan Devine, Castletanna (IE); Cornelis Wilhelmus Maria Bastiaansen, Burgemeester Geurtsweg (NL); Jean-Pierre Teunissen, Margarethastraat (NL); Martin Cloonan, Craughwell (IE); Clement L. Higginbotham, Athlone (IE)

(73) Assignee: Transitions Optical, Inc., Pinellas Park, FL (US)

( * ) Notice: Subject to any disclaimer, the term of this patent is extended or adjusted under 35 U.S.C. 154(b) by 2125 days.

(21) Appl. No.: 11/779,386

(22) Filed: Jul. 18, 2007

(65) Prior Publication Data
US 2007/0291345 A1 Dec. 20, 2007

Related U.S. Application Data

(63) Continuation-in-part of application No. 10/846,650, filed on May 17, 2004, now Pat. No. 7,256,921.

(60) Provisional application No. 60/821,028, filed on Aug. 1, 2006, provisional application No. 60/484,100, filed on Jul. 1, 2003.

(51) Int. Cl.
*B29C 55/12* (2006.01)
*G01N 21/19* (2006.01)
*G02B 5/23* (2006.01)
*G02B 5/30* (2006.01)
*G03C 1/73* (2006.01)
*G02F 1/1335* (2006.01)

(52) U.S. Cl.
CPC ............... *B29C 55/12* (2013.01); *G01N 21/19* (2013.01); *G02B 5/23* (2013.01); *G02B 5/305* (2013.01); *G03C 1/733* (2013.01); *B29K 2995/0034* (2013.01); *G02F 1/133533* (2013.01); *G02F 2202/14* (2013.01)

(58) Field of Classification Search
CPC .......... B29C 55/12; B29K 2995/0034; G01N 21/19; G02B 5/23; G02B 5/305; G02F 1/133533; G02F 2202/14; G03C 1/733
See application file for complete search history.

(56) References Cited

U.S. PATENT DOCUMENTS

| | | |
|---|---|---|
| 2,319,826 A | 5/1943 | Pellett |
| 2,334,446 A | 11/1943 | Serrell |
| 2,475,921 A | 7/1949 | Smith |
| 2,481,830 A | 9/1949 | Dreyer |
| 2,544,659 A | 3/1951 | Dreyer |
| 3,276,316 A | 10/1966 | Makas |
| 3,361,706 A | 1/1968 | Meriwether et al. |
| 3,653,863 A | 4/1972 | Araujo |
| 4,039,254 A | 8/1977 | Harsch |
| 4,043,637 A | 8/1977 | Hovey |
| 4,166,043 A | 8/1979 | Uhlmann et al. |
| 4,190,330 A | 2/1980 | Berreman |
| 4,279,474 A | 7/1981 | Belgorod |
| 4,367,170 A | 1/1983 | Uhlmann et al. |
| 4,549,894 A | 10/1985 | Araujo et al. |
| 4,556,605 A | 12/1985 | Mogami et al. |
| 4,637,896 A | 1/1987 | Shannon |
| 4,648,925 A | 3/1987 | Goepfert et al. |
| 4,685,783 A | 8/1987 | Heller et al. |
| 4,728,173 A | 3/1988 | Toth |
| 4,756,605 A | 7/1988 | Okada et al. |
| 4,756,973 A | 7/1988 | Sakagami et al. |
| 4,810,433 A | 3/1989 | Takayanagi et al. |
| 4,838,673 A | 6/1989 | Richards et al. |
| 4,863,763 A | 9/1989 | Takeda et al. |
| 4,865,668 A | 9/1989 | Goepfert et al. |
| 4,873,026 A | 10/1989 | Behre et al. |
| 4,873,029 A | 10/1989 | Blum |
| 4,931,220 A | 6/1990 | Haynes et al. |
| 4,974,941 A | 12/1990 | Gibbons et al. |
| 4,977,028 A | 12/1990 | Goepfert et al. |

(Continued)

FOREIGN PATENT DOCUMENTS

| | | |
|---|---|---|
| EP | 0321563 | 1/1988 |
| EP | 0313941 A1 | 3/1989 |
| EP | 0 488 164 A2 | 3/1992 |
| EP | 0446717 A2 | 3/1992 |
| EP | 0 543 678 A1 | 5/1993 |
| EP | 0 397 263 B1 | 12/1994 |
| EP | 0686685 B1 | 12/1995 |
| EP | 0770116 | 2/1997 |
| EP | 0 331 233 B1 | 4/1997 |
| EP | 0 772 069 A1 | 7/1997 |
| EP | 1 162 482 A2 | 12/2001 |

(Continued)

OTHER PUBLICATIONS

"Cholesteric Filters and Films" Rolic Ltd. available at http://www.rolic.com/050application/05223content.htm, 2 pages (2003).

(Continued)

*Primary Examiner* — Callie Shosho
*Assistant Examiner* — John Freeman
(74) *Attorney, Agent, or Firm* — The Webb Law Firm

(57) ABSTRACT

Provided is an oriented polymeric sheet comprising a photochromic-dichroic material, wherein the sheet exhibits dichroism in an activated state. Also provided is a multilayer composite comprising at least a support layer; and an oriented thermoplastic polymeric sheet having two opposing surfaces and comprising a photochromic-dichroic material. The sheet exhibits dichroism in an activated state. At least one surface of the sheet is connected to at least a portion of the support layer. The present invention also relates to an optical element comprising the multilayer composite. Related methods also are disclosed.

30 Claims, No Drawings

(56) References Cited

U.S. PATENT DOCUMENTS

| | | | |
|---|---|---|---|
| 5,067,795 A | 11/1991 | Senatore | |
| 5,073,294 A | 12/1991 | Shannon et al. | |
| 5,130,058 A | 7/1992 | Tanaka et al. | |
| 5,130,353 A | 7/1992 | Fischer et al. | |
| 5,139,707 A | 8/1992 | Guglielmetti et al. | |
| 5,155,607 A | 10/1992 | Inoue et al. | |
| 5,166,345 A | 11/1992 | Akashi et al. | |
| 5,180,470 A | 1/1993 | Smith et al. | |
| 5,185,390 A | 2/1993 | Fischer et al. | |
| 5,189,448 A | 2/1993 | Yaguchi | |
| 5,200,116 A | 4/1993 | Heller | |
| 5,202,053 A | 4/1993 | Shannon | |
| 5,204,850 A | 4/1993 | Obata | |
| 5,236,958 A | 8/1993 | Miyashita | |
| 5,247,377 A | 9/1993 | Omeis et al. | |
| 5,252,742 A | 10/1993 | Miyashita | |
| 5,289,547 A | 2/1994 | Ligas et al. | |
| 5,359,085 A | 10/1994 | Iwamoto et al. | |
| 5,389,698 A | 2/1995 | Chigrinov et al. | |
| 5,464,669 A | 11/1995 | Kang et al. | |
| 5,488,119 A | 1/1996 | Fischer-Reimann et al. | |
| 5,543,267 A | 8/1996 | Stumpe et al. | |
| 5,602,661 A | 2/1997 | Schadt et al. | |
| 5,608,567 A | 3/1997 | Grupp | |
| 5,641,846 A | 6/1997 | Bieringer et al. | |
| 5,644,416 A | 7/1997 | Morikawa et al. | |
| 5,645,767 A | 7/1997 | Van Gemert | |
| 5,658,501 A | 8/1997 | Kumar et al. | |
| 5,698,141 A | 12/1997 | Kumar | |
| 5,723,072 A | 3/1998 | Kumar | |
| 5,746,949 A | 5/1998 | Shen et al. | |
| 5,821,287 A | 10/1998 | Hu et al. | |
| 5,846,452 A | 12/1998 | Gibbons et al. | |
| 5,867,316 A | 2/1999 | Carlson et al. | |
| 5,882,774 A | 3/1999 | Jonza et al. | |
| 5,903,330 A | 5/1999 | Fünfschilling et al. | |
| 5,943,104 A | 8/1999 | Moddel et al. | |
| 5,952,515 A | 9/1999 | Melzig et al. | |
| 5,962,617 A | 10/1999 | Slagel | |
| 6,022,497 A | 2/2000 | Kumar | |
| 6,025,026 A | 2/2000 | Smith et al. | |
| 6,036,890 A | 3/2000 | Melzig et al. | |
| 6,049,428 A | 4/2000 | Khan et al. | |
| 6,060,001 A | 5/2000 | Welch et al. | |
| 6,080,338 A | 6/2000 | Kumar | |
| 6,096,375 A | 8/2000 | Ouderkirk et al. | |
| 6,113,814 A | 9/2000 | Gemert et al. | |
| 6,136,968 A | 10/2000 | Chamontin et al. | |
| 6,150,430 A | 11/2000 | Walters et al. | |
| 6,153,126 A | 11/2000 | Kumar | |
| 6,160,597 A | 12/2000 | Schadt et al. | |
| 6,187,444 B1 | 2/2001 | Bowles, III et al. | |
| 6,239,778 B1 | 5/2001 | Palffy-Muhoray et al. | |
| 6,245,399 B1 | 6/2001 | Sahouani et al. | |
| 6,268,055 B1 | 7/2001 | Walters et al. | |
| 6,281,366 B1 | 8/2001 | Frigoli et al. | |
| 6,284,418 B1 | 9/2001 | Trantolo | |
| 6,296,785 B1 | 10/2001 | Nelson et al. | |
| 6,312,811 B1 | 11/2001 | Frigoli et al. | |
| 6,334,681 B1 | 1/2002 | Perrott et al. | |
| 6,338,808 B1 | 1/2002 | Kawata et al. | |
| 6,348,604 B1 | 2/2002 | Nelson et al. | |
| 6,353,102 B1 | 3/2002 | Kumar | |
| 6,369,869 B2 | 4/2002 | Schadt et al. | |
| 6,432,544 B1 | 8/2002 | Stewart et al. | |
| 6,433,043 B1 | 8/2002 | Misura et al. | |
| 6,436,525 B1 | 8/2002 | Welch et al. | |
| 6,474,695 B1 | 11/2002 | Schneider et al. | |
| 6,506,488 B1 | 1/2003 | Stewart et al. | |
| 6,531,076 B2 | 3/2003 | Crano et al. | |
| 6,555,028 B2 | 4/2003 | Walters et al. | |
| 6,579,422 B1 | 6/2003 | Kakinuma | |
| 6,597,422 B1 | 7/2003 | Fünfschilling et al. | |
| 6,602,603 B2 | 8/2003 | Welch et al. | |
| 6,613,433 B2 | 9/2003 | Yamamoto et al. | |
| 6,630,597 B1 | 10/2003 | Lin et al. | |
| 6,641,874 B2 | 11/2003 | Kuntz et al. | |
| 6,690,495 B1 * | 2/2004 | Kosa et al. | 349/86 |
| 6,705,569 B1 | 3/2004 | Sanders et al. | |
| 6,717,644 B2 | 4/2004 | Schadt et al. | |
| 6,808,657 B2 | 10/2004 | Fansler et al. | |
| 6,844,686 B1 | 1/2005 | Schneck et al. | |
| 7,349,137 B2 * | 3/2008 | Kumar et al. | 359/241 |
| 7,505,189 B2 * | 3/2009 | Kumar et al. | 359/241 |
| 7,847,998 B2 * | 12/2010 | Kumar et al. | 359/241 |
| 8,089,678 B2 * | 1/2012 | Kumar et al. | 359/241 |
| 2002/0006505 A1 * | 1/2002 | Nishizawa et al. | 428/220 |
| 2002/0039627 A1 | 4/2002 | Ichihashi et al. | |
| 2002/0090516 A1 | 7/2002 | Loshak et al. | |
| 2002/0136899 A1 * | 9/2002 | deRojas et al. | 428/412 |
| 2002/0167639 A1 | 11/2002 | Coates et al. | |
| 2002/0180916 A1 | 12/2002 | Schadt et al. | |
| 2003/0008958 A1 | 1/2003 | Momoda et al. | |
| 2003/0045612 A1 | 3/2003 | Misura et al. | |
| 2003/0189684 A1 | 10/2003 | Kuntz et al. | |
| 2004/0090570 A1 | 5/2004 | Kosa et al. | |
| 2004/0158028 A1 | 8/2004 | Bühler | |
| 2004/0223221 A1 | 11/2004 | Sugmura et al. | |
| 2005/0003107 A1 | 1/2005 | Kumar et al. | |
| 2005/0004361 A1 | 1/2005 | Kumar et al. | |
| 2005/0012998 A1 | 1/2005 | Kumar et al. | |
| 2005/0146680 A1 | 7/2005 | Muisener et al. | |
| 2005/0151926 A1 | 7/2005 | Kumar et al. | |
| 2005/0196617 A1 | 9/2005 | King | |
| 2006/0022176 A1 | 2/2006 | Wang et al. | |
| 2008/0112049 A1 | 5/2008 | Umemoto et al. | |

FOREIGN PATENT DOCUMENTS

| | | |
|---|---|---|
| EP | 1184379 A1 | 6/2002 |
| EP | 1 203 967 A1 | 8/2002 |
| EP | 1 394 595 A1 | 3/2004 |
| EP | 1 560 060 A1 | 3/2005 |
| GB | 583842 | 1/1947 |
| GB | 2 169417 A | 9/1986 |
| JP | 59 135428 A | 3/1984 |
| JP | 64-090286 | 4/1989 |
| JP | 03-200118 | 2/1991 |
| JP | 03-200118 A | 2/1991 |
| JP | 07-062337 A | 3/1995 |
| WO | WO 89/11674 A1 | 3/1989 |
| WO | WO 96/01884 A1 | 1/1996 |
| WO | WO 97/05213 | 2/1997 |
| WO | WO 97/22894 | 6/1997 |
| WO | WO 98/19207 | 7/1998 |
| WO | WO 99/20630 | 4/1999 |
| WO | WO 00/19252 | 6/2000 |
| WO | WO 00/77559 A1 | 12/2000 |
| WO | WO 01/02449 | 1/2001 |
| WO | WO 01/55960 A1 | 2/2001 |
| WO | WO 02/058921 A1 | 1/2002 |
| WO | WO 02/29489 A2 | 11/2002 |
| WO | WO 03/032066 A1 | 4/2003 |
| WO | WO 03/019270 | 6/2003 |
| WO | WO 2004/003107 A1 | 1/2004 |
| WO | WO 2004/041961 A1 | 5/2004 |
| WO | WO 2005/084826 A1 | 9/2005 |
| WO | WO 2005/085912 A1 | 9/2005 |
| WO | WO 2006/094313 A2 | 9/2006 |

OTHER PUBLICATIONS

"Dichroic Linear Polarisers" Rolic Ltd. Available at http://www.rolic.com/050application/05313content.htm 1 page (2003).
Bachels, Thomas, et al., "Novel Photo-Aligned LC-Polymer Wide View Film for TN Displays," *Eurodisplay*, (2002), pp. 183-186.
Castellano, Joseph A. "Surface Anchoring of Liquid Crystal Molecules on Various Substrates " *Mol. Cryst. Liq. Cryst.*, vol. 94, pp. 33-41 (1983).
Chigrinov, V.G. and Kozenkov, V.M., "New Results on Liquid Crystal Alignment by Photopolymerization," *Proceedings of the SPIE—The Internationali Society for Optical Engineering*, SPIE vol. 2408 pp. 130-140 (1995).

(56) References Cited

OTHER PUBLICATIONS

Dyadyusha, A.G. et al. "Light-Induced Planar Orientation of a Nematic Liquid Crystal on an Anisotropic Surface without Microrelief," *Ukr. Fiz. Zhurn*, (Ukraine), vol. 35, No. 5, pp. 1059-1062.

Hikmet, R.A.M and de Witz, C., "Gel Layers for Inducting Adjustable Pretilt Angles in Liquid Crystal Systems," *J. App. Phys*. vol. 70, No. 3, pp. 1265-1266 (Aug. 1991).

Huang, D.D. et al. "Effect of Aligning Layer Thickness on Photo-Aligned Ferroelectric Liquid Crystal Displays "*Proceedings of the $6^{th}$ Chinese Optoelectronics Symposium, Hong Kong China*, IEEE (New York), pp. 231-234 (2003).

Kozenkov, V.M., Chigrinov, V.G., and Kwok, H.S. "Photoanisotropic Effects in Poly (Vinyl-Cinnamate) Derivatives and Their Applications " *Mol. Cryst. Lila. Cryst.*, vol. 409, pp. 251-267 (2004).

Kvasnikov, E.D., Kozenkov, V.M., and Barachevskii, V.A., "Birefringence in Polyvinylcinnamate Films Induced by Polarized Light," *Doklady Akademii nauk SSSR*, vol. 237, No. 3, USSR pp. 633-636 (1977).

Moia, Franco et al. "Optical LLP/LCP Devices: A New Generation of Optical Security Elements," *Proceedings of SPIE: Optical Security and Counterfeit Deterrence Techniques III*, vol. 3973 (2000), pp. 196-203, San Jose (CA), Jan. 27-28, 2000.

Moia, Franco, "New Coloured Optical Security Elements Using Rolic's LPP/LCP Technology: Devices for 1st to 3rd Level Inspection " *Proceedings of SPIE: Optical Security and Counterfeit Deterrence Techniques IV*, vol. 4677 (2002), pp. 194-202, San Jose (CA) Jan. 23-25, 2002.

Schadt, Martin "Liquid Crystal Displays and Novel Optical Thin Films Enabled by Photo-Alignment," Mol. Cryst. Liq. Cryst. vol. 364, pp. 151-169 (2001).

Schadt, Martin "Optics and Applications of Photo-Aligned Liquid Crystalline Surfaces," Nonlinear Optics, vol. 25, pp. 1-12 (2000).

Schadt, Martin et al. "Surface-Induced Parallel Alignment of Liquid Crystals by Linearly Polymerized Photopolymers," Jpn. J. Appl. Phys. vol. 31, No. 7, pp. 2155-2164 (Jul. 1992).

Seiberle, Hubert et al., "Invited Paper: Photo-Aligned Anisotroipc Optical Thin Films," SID 03 Digest, Society of Information Displays (2003), pp. 1162-1165.

\* cited by examiner

ORIENTED POLYMERIC SHEETS EXHIBITING DICHROISM AND ARTICLES CONTAINING THE SAME

CROSS-REFERENCE TO RELATED APPLICATIONS

This application claims the benefit of priority of U.S. Provisional patent Application No. 60/821,028 filed Aug. 1, 2006 and is a continuation-in-part of U.S. patent application Ser. No. 10/846,650 filed May 17, 2004 now U.S. Pat. No. 7,256,921 which claims the benefit of priority of U.S. Provisional Patent Application No. 60/484,100 filed Jul. 1, 2003.

FIELD OF THE INVENTION

The present invention relates to an oriented polymeric sheet including photochromic dichroic materials which is useful as a component in a multilayer composite, for example, an optical article.

BACKGROUND OF THE INVENTION

Conventional, linearly polarizing elements, such as linearly polarizing lenses for sunglasses and linearly polarizing filters, are typically formed from stretched polymer sheets containing a dichroic material, such as a dichroic dye. Consequently, conventional linearly polarizing elements are static elements having a single, linearly polarizing state. Accordingly, when a conventional linearly polarizing element is exposed to either randomly polarized radiation or reflected radiation of the appropriate wavelength, some percentage of the radiation transmitted through the element will be linearly polarized. As used herein the term "linearly polarize" means to confine the vibrations of the electric vector of light waves to one direction or plane.

Further, conventional linearly polarizing elements are typically tinted. That is, conventional linearly polarizing elements can contain a coloring agent (i.e., the dichroic material) and have an absorption spectrum that does not vary in response to actinic radiation. As used herein "actinic radiation" means electromagnetic radiation, such as but not limited to ultraviolet and visible radiation that is capable of causing a response. The color of the conventional linearly polarizing element will depend upon the coloring agent used to form the element, and most commonly, is a neutral color (for example, brown or gray). Thus, while conventional linearly polarizing elements are useful in reducing reflected light glare, because of their tint, they are not well suited for use under certain low-light conditions. Further, because conventional linearly polarizing elements have only a single, tinted linearly polarizing state, they can be limited in their ability to store or display information.

As discussed above, conventional linearly polarizing elements may be formed using sheets of stretched polymer films containing a dichroic material. As used herein the term "dichroic" means capable of absorbing one of two orthogonal plane polarized components of at least transmitted radiation more strongly than the other. Thus, while dichroic materials are capable of preferentially absorbing one of two orthogonal plane polarized components of transmitted radiation, if the molecules of the dichroic material are not suitably positioned or arranged, no net linear polarization of transmitted radiation will be achieved. That is, due to the random positioning of the molecules of the dichroic material, selective absorption by the individual molecules will cancel each other such that no net or overall linear polarizing effect is achieved. Thus, it is generally necessary to suitably position or arrange the molecules of the dichroic material in order to achieve a net linear polarization.

One common method of aligning the molecules of a dichroic dye involves heating a sheet or layer of polyvinyl alcohol ("PVA") to soften the PVA and then stretching the sheet to orient the PVA polymer chains. Thereafter, the dichroic dye is impregnated into the stretched sheet and dye molecules take on the orientation of the polymer chains. That is, the dye molecules become aligned such that the long axis of the dye molecule are generally parallel to the oriented polymer chains. Alternatively, the dichroic dye can be first impregnated into the PVA sheet, and thereafter the sheet can be heated and stretched as described above to orient the PVA polymer chains and associated dye. In this manner, the molecules of the dichroic dye can be suitably positioned or arranged within the oriented polymer chains of the PVA sheet and a net linear polarization can be achieved. That is, the PVA sheet can be made to linearly polarize transmitted radiation, or in other words, a linearly polarizing filter can be formed.

In contrast to the dichroic elements discussed above, conventional photochromic elements, such as photochromic lenses that are formed using conventional thermally reversible photochromic materials are generally capable of converting from a first state, for example a "clear state," to a second state, for example a "colored state," in response to actinic radiation, and reverting back to the first state in response to thermal energy. As used herein the term "photochromic" means having an absorption spectrum for at least visible radiation that varies in response to at least actinic radiation. Thus, conventional photochromic elements are generally well suited for use in both low-light and bright conditions. However, conventional photochromic elements that do not include linearly polarizing filters are generally not adapted to linearly polarize radiation. That is, the absorption ratio of conventional photochromic elements, in either state, is generally less than two. As used herein the term "absorption ratio" refers to the ratio of the absorbance of radiation linearly polarized in a first plane to the absorbance of the same wavelength radiation linearly polarized in a plane orthogonal to the first plane, wherein the first plane is taken as the plane with the highest absorbance. Therefore, conventional photochromic elements cannot reduce reflected light glare to the same extent as conventional linearly polarizing elements. Further, as previously mentioned, conventional photochromic elements may have a limited ability to store or display information.

Accordingly, it would be advantageous to provide elements and devices that are adapted to display both linearly polarizing and photochromic properties. Further, it would be advantageous to provide elements and devices that are adapted to display linear, circular or elliptical polarization as well as photochromic properties.

SUMMARY OF THE INVENTION

The present invention is directed to an oriented polymeric sheet comprising a photochromic-dichroic material, wherein the sheet exhibits dichroism in an activated state.

In a further embodiment, the present invention is directed to a multilayer composite comprising at least a support layer; and an oriented thermoplastic polymeric sheet having two opposing surfaces and comprising a photochromic-dichroic material. The sheet exhibits dichroism in an activated state. At least one surface of the sheet is connected to at least a portion of the support layer.

The present invention also relates to an optical element comprising the multilayer composite described above.

In a further embodiment, the present invention is directed to an oriented polymeric sheet comprising a photchromic-dichroic material, said sheet having a first ordered region having a first general direction, and at least one second ordered region adjacent the first ordered region having a second general direction that is different from the first general direction, wherein the sheet exhibits dichroism in an activated state.

Related methods also are disclosed.

DETAILED DESCRIPTION OF THE INVENTION

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

The present invention is directed to an oriented thermoplastic polymeric sheet comprising a photochromic-dichroic material, wherein the sheet exhibits dichroism (i.e., linear polarization) in at least an activated state. The oriented thermoplastic polymeric sheet of the present invention exhibits a first state and a second state. The photochromic-dichroic material comprising the sheet is adapted to transition from a first state to a second state in response to at least actinic radiation, to revert back to the first state in response to thermal energy, and to linearly polarize at least transmitted radiation in at least one of the first state and the second state. As used herein, the term "thermal energy" means any form of heat.

The term "photochromic-dichroic" means displaying both photochromic and dichroic (i.e., linearly polarizing) properties under certain conditions, which properties are at least detectable by instrumentation. Accordingly, "photochromic-dichroic compounds" are compounds displaying both photochromic and dichroic (i.e., linearly polarizing) properties under certain conditions, which properties are at least detectable by instrumentation. Thus, photochromic-dichroic compounds have an absorption spectrum for at least visible radiation that varies in response to at least actinic radiation, and are capable of absorbing one of two orthogonal plane polarized components of at least transmitted radiation more strongly than the other (i.e., capable of exhibiting dichroism). Additionally, as with conventional photochromic compounds discussed below, the photochromic-dichroic compounds disclosed herein can be thermally reversible. That is, the photochromic-dichroic compounds can switch from a first state to a second state in response to actinic radiation and revert back to the first state in response to thermal energy. As used herein the term "compound" means a substance formed by the union of two or more elements, components, ingredients, or parts and includes, without limitation, molecules and macromolecules (for example polymers and oligomers) formed by the union of two or more elements, components, ingredients, or parts.

For example, according to various non-limiting embodiments disclosed herein, the photochromic-dichroic compound can have a first state having a first absorption spectrum, a second state having a second absorption spectrum that is different from the first absorption spectrum, and can be adapted to switch from the first state to the second state in response to at least actinic radiation and to revert back to the first state in response to thermal energy. Further, the photochromic-dichroic compound can be dichroic (i.e., linearly polarizing) in one or both of the first state and the second state. For example, although not required, the photochromic-dichroic compound can be linearly polarizing in an activated state and non-polarizing in the bleached or faded (i.e., not activated) state. As used herein, the term "activated state" refers to the photochromic-dichroic compound when exposed to sufficient actinic radiation to cause at least a portion of the photochromic-dichroic compound to switch from a first state to a second state. Further, although not required, the photochromic-dichroic compound can be dichroic in both the first and second states. While not limiting herein, for example, the photochromic-dichroic compound can linearly polarize visible radiation in both the activated state and the bleached state. Further, the photochromic-dichroic compound can linearly polarize visible radiation in an activated state, and can linearly polarize UV radiation in the bleached state.

The term "oriented" as used in conjunction with the polymeric sheet of the present invention, means that the sheet has at least a first general direction (of alignment) such that one or more other structures or components comprising the sheet are positioned or suitably arranged along that same general direction. For example, the alignment or ordering of the photochromic-dichroic compounds along the long-axis of the photochromic-dichroic compound in the activated state is essentially parallel to at least the first general direction of the sheet. As used herein with reference to order or alignment of a material or structure, the term "general direction" refers to the predominant arrangement or orientation of the material, compound or structure. Further, it will be appreciated by those skilled in the art that a material, compound or structure can have a general direction even though there is some variation within the arrangement of the material, compound or structure, provided that the material, compound or structure has at least one predominate arrangement.

As discussed above, the oriented thermoplastic polymeric sheets according to various non-limiting embodiments disclosed herein can have at least a first general direction. For example, the sheet can comprise a first ordered region having a first general direction and at least one second ordered region adjacent to the first ordered region having a second general direction that is different from the first general direction. Further, the sheet can have a plurality of ordered regions, each of which has a general direction that is the same or different from the remaining regions so as to form a desired pattern or design.

The present invention, in one embodiment, is directed to a method for forming at least a two-directional pattern (as described immediately above) in a polymeric sheet comprising a photochromic-dichroic material, said sheet exhibiting dichroism in an activated state, said method comprising stretching the polymeric sheet biaxially in two or more sequential stages.

Also, as used herein, the term "coating" means a supported film derived from a flowable composition, which may or may not have a uniform thickness, and specifically excludes polymeric sheets. By contrast, the term "sheet" means a pre-formed film having a generally uniform thickness and capable of self-support. For purposes of the present invention, the term "sheet" is intended to include a "fiber" which is pre-formed, and has a measurable, generally uniform thickness. The sheet has two opposing surfaces (including sheet in the form of a fiber) either or both of which may or may not have thereover one or more layers (including coating layers). Any of the layers can comprise inorganic and/or organic materials.

The polymeric sheet of the present invention can have an absorption ratio of at least 1.5 in the activated state, for example the polymeric sheet can have an absorption ratio in the activated state ranging from 1.5 to 30, or ranging from 3 to 20, or from 4 to 10, such as 5. The absorption ratio is determined according to the ABSORPTION RATIO TEST METHOD as described hereinbelow with respect to the examples.

The polymeric sheet can comprise a polymeric composition of any of a wide variety of polymers, including both thermosetting polymers and thermoplastic polymers. As used herein, the term "polymer" is intended to include both polymers and oligomers, as well as both homopolymers and copolymers. Such polymers can include, for example, acrylic polymers, polyester polymers, polyurethane polymers, poly (urea)urethane polymers, polyamine polymers, polyepoxide polymers, polyamide polymers, polyether polymers, polysiloxane polymers, polysulfide polymers, copolymers thereof, and mixtures thereof. Generally these polymers can be any polymers of these types made by any method known to those skilled in the art.

The polymers used to form the polymeric sheet also may comprise functional groups including, but not limited to, carboxylic acid groups, amine groups, epoxide groups, hydroxyl groups, thiol groups, carbamate groups, amide groups, urea groups, isocyanate groups (including blocked isocyanate groups) mercaptan groups, groups having ethylenic unsaturation (e.g., acrylate groups), vinyl groups, and combinations thereof. Appropriate mixtures of film-forming resins may also be used in the preparation of the coating compositions. If the polymer composition from which the polymeric sheet is formed comprises functional group-containing polymers (such as any of the previously mentioned functional group-containing polymers), the polymer composition can further comprise a material having functional groups reactive with those of said polymer. Reaction may be facilitated, for example, by thermal, photoinitiated, oxidative, and/or radiative curing techniques. Also contemplated are mixtures of any of the foregoing polymers.

Further non-limiting examples of polymers suitable for use in forming the polymeric sheet of the present invention are the thermoplastic block copolymers of polyalkyl(meth)acrylate and polyamide described in Published U.S. Patent Application 2004/0068071 A1 at paragraphs [0020]-[0042], the specified portions of which is incorporated by reference herein; and U.S. Pat. No. 6,096,375 at column 18, line 8 to column 19, line 5, the specified portions of which are incorporated by reference herein.

In a particular embodiment of the present invention, the polymeric sheet comprises an elastomeric polymer, for example thermoplastic elastomeric polymers. As used herein, by "elastomeric polymer" is meant a polymer that has a high degree of resiliency and elasticity such that it is capable of at least partially reversible deformation or elongation. In some instances, when stretched, the molecules of an elastomer are aligned and can take on aspects of a crystalline arrangement; and upon release, the elastomer can, to some extent, return to its natural disordered state. For purposes of the present invention, elastomeric polymers can include thermoplastic, thermoplastic elastomeric polymers, and thermosetting polymers provided such polymers fall within the description provided above for "elastomeric polymer".

The elastomeric polymer can comprise any of wide variety of art recognized elastomers including but not limited to copolymers of any of the previously mentioned polymers. In an embodiment of the present invention, the elastomeric polymer can comprise a block copolymer having ether and/or ester linkages in the polymer backbone. Examples of suitable block copolymers can include, but are not limited to, poly (amide-ether) block copolymers, poly(ester-ether) block copolymers, poly(ether-urethane) block copolymers, poly (ester-urethane) block copolymers, and/or poly(ether-urea) block copolymers. Suitable specific examples of such elastomeric polymers can include, but are not limited to, those commercially available under the tradenames DESMOPAN® and TEXIN® from Bayer Material Science; ARNITEL® from Royal DSM; and PEBAX® from Atofina Chemicals or Cordis Corporation.

As previously mentioned, the oriented polymeric sheet of the present invention comprises a photochromic-dichroic material. Any of the photochromic-dichroic materials well known in the art are suitable for this purpose. Examples of suitable photochromic-dichroic compounds are those that comprise: (a) at least one photochromic group (PC) chosen from pyrans, oxazines, and fulgides; and (b) at least one lengthening agent attached to the at least one photochromic group, wherein the lengthening agent (L) is represented by the following Formula I (which is described in detail below):

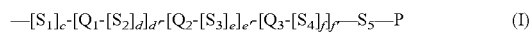

—[S$_1$]$_c$-[Q$_1$-[S$_2$]$_d$]$_{d'}$-[Q$_2$-[S$_3$]$_e$]$_{e'}$-[Q$_3$-[S$_4$]$_f$]$_{f'}$—S$_5$—P    (I)

As used herein, the term "attached" means directly bonded to or indirectly bonded to through another group. Thus, for example, according to various non-limiting embodiments disclosed herein, L can be directly bonded to PC as a substituent on PC, or L can be a substituent on another group (such as a group represented by R$^1$, which is discussed below) that is directly bonded to PC (i.e., L is indirectly bonded to PC). Although not limiting herein, according to various non-limiting embodiments, L can be attached to PC so as to extend or lengthen PC in an activated state such that the absorption ratio of the extended PC (i.e., the photochromic compound) is enhanced as compared to PC alone. Although not limiting herein, according to various non-limiting embodiments, the location of attachment of L on PC can be chosen such that L lengthens PC in at least one of a direction parallel to and a direction perpendicular to a theoretical transitional dipole moment of the activated form of PC. As used herein the term "theoretical transitional dipole moment" refers to transient dipolar polarization created by interaction of electromagnetic radiation with the molecule. See, for example, *IUPAC Compendium of Chemical Technology*, 2$^{nd}$ Ed., International Union of Pure and Applied Chemistry (1997).

With reference to Formula I above, each Q$_1$, Q$_2$, and Q$_3$ can be independently chosen for each occurrence from: a divalent group chosen from an unsubstituted or a substituted aromatic group, an unsubstituted or a substituted alicyclic group, an unsubstituted or a substituted heterocyclic group, and mixtures thereof, wherein substituents are chosen from: a group represented by P (as set forth below), aryl, thiol, amide, liquid crystal mesogens, halogen, C$_1$-C$_{18}$alkoxy, poly(C$_1$-C$_{18}$ alkoxy), amino, amino(C$_1$-C$_{18}$)alkylene, C$_1$-C$_{18}$alkylamino, di-(C$_1$-C$_{18}$)alkylamino, C$_1$-C$_{18}$ alkyl, C$_2$-C$_{18}$ alkene, C$_2$-C$_{18}$ alkyne, C$_1$-C$_{18}$ alkyl(C$_1$-C$_{18}$)alkoxy, C$_1$-C$_{18}$ alkoxycarbonyl, $C_1$-$C_{18}$ alkylcarbonyl, $C_1$-$C_{18}$ alkyl carbonate, aryl carbonate, $C_1$-$C_{18}$ acetyl, $C_3$-$C_{10}$cycloalkyl, $C_3$-$C_{10}$cycloalkoxy, isocyanato, amido, cyano, nitro, a straight-chain or branched $C_1$-$C_{18}$ alkyl group that is mono-substituted with cyano, halo, or $C_1$-$C_{18}$ alkoxy, or poly-substituted with halo, and a group represented by one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M. As used herein, the prefix "poly" means at least two.

As discussed above, $Q_1$, $Q_2$, and $Q_3$ can be independently chosen for each occurrence from a divalent group, such as an unsubstituted or a substituted aromatic group, unsubstituted or substituted heterocyclic group, and an unsubstituted or substituted alicylic group. Non-limiting examples of useful aromatic groups include: benzo, naphtho, phenanthro, biphenyl, tetrahydro naphtho, terphenyl, and anthraceno.

As used herein the term "heterocyclic group" means a compound having a ring of atoms, wherein at least one atom forming the ring is different than the other atoms forming the ring. Further, as used herein, the term heterocyclic group specifically excludes fused heterocyclic groups. Non-limiting examples of suitable heterocyclic groups from which $Q_1$, $Q_2$, and $Q_3$ can be chosen include: isosorbitol, dibenzofuro, dibenzothieno, benzofuro, benzothieno, thieno, furo, dioxino, carbazolo, anthranilyl, azepinyl, benzoxazolyl, diazepinyl, dioazlyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrroyl, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinuclidinyl, quinolyl, thiazolyl, triazolyl, triazyl, N-arylpiperazino, aziridino, arylpiperidino, thiomorpholino, tetrahydroquinolino, tetrahydroisoquinolino, pyrryl, unsubstituted, mono- or di-substituted $C_4$-$C_{18}$ spirobicyclic amines, and unsubstituted, mono- or di-substituted $C_4$-$C_{18}$ spirotricyclic amines.

As discussed above, $Q_1$, $Q_2$, and $Q_3$ can be chosen from mono- or di-substituted $C_4$-$C_{18}$ spirobicyclic amine and $C_4$-$C_{18}$ spirotricyclic amine. Non-limiting examples of suitable substituents include aryl, $C_1$-$C_6$ alkyl, $C_1$-$C_6$ alkoxy or phenyl ($C_1$-$C_6$)alkyl. Specific non-limiting examples of mono- or di-substituted spirobicyclic amines include: 2-azabicyclo[2.2.1]hept-2-yl; 3-azabicyclo[3.2.1]oct-3-yl; 2-azabicyclo[2.2.2]oct-2-yl; and 6-azabicyclo[3.2.2]nonan-6-yl. Specific non-limiting examples of mono- or di-substituted tricyclic amines include: 2-azatricyclo[3.3.1.1(3,7)]decan-2-yl; 4-benzyl-2-azatricyclo[3.3.1.1(3,7)]decan-2-yl; 4-methoxy-6-methyl-2-azatricyclo[3.3.1.1(3,7)]decan-2-yl; 4-azatricyclo[4.3.1.1(3,8)]undecan-4-yl; and 7-methyl-4-azatricyclo[4.3.1.1(3,8)]undecan-4-yl. Examples of alicyclic groups from which $Q_1$, $Q_2$, and $Q_3$ can be chosen include, without limitation, cyclohexyl, cyclopropyl, norbornenyl, decalinyl, adamantanyl, bicycloctane, per-hydrofluorene, and cubanyl.

With continued reference to Formula I, and each $S_1$, $S_2$, $S_3$, $S_4$, and $S_5$ is independently chosen for each occurrence from a spacer unit chosen from:

(1) —(CH$_2$)$_g$—, —(CF$_2$)$_h$—, —Si(CH$_2$)$_g$—, —Si[(CH$_3$)$_2$]O)$_h$—, wherein g is independently chosen for each occurrence from 1 to 20; h is chosen from 1 to 16;

(2) —N(Z)—, —C(Z)=C(Z)—, —C(Z)=N—, —C(Z')—C(Z')—, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and (3) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;

provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other. As used herein the term "heteroatom" means atoms other than carbon or hydrogen.

Further, in Formula I, according to various non-limiting embodiments, c, d, e, and f each can be independently chosen from an integer ranging from 1 to 20, inclusive; and d', e' and f' each can be independently chosen from 0, 1, 2, 3, and 4, provided that the sum of d'+e'+f' is at least 1. According to other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 2. According to still other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 3. According to still other non-limiting embodiments, c, d, e, and f each can be independently chosen from an integer ranging from 0 to 20, inclusive; and d', e' and f' each can be independently chosen from 0, 1, 2, 3, and 4, provided that the sum of d'+e'+f' is at least 1.

Further, in Formula I, P can be chosen from: aziridinyl, hydrogen, hydroxy, aryl, alkyl, alkoxy, amino, alkylamino, alkylalkoxy, alkoxyalkoxy, nitro, polyalkyl ether, ($C_1$-$C_6$) alkyl($C_1$-$C_6$)alkoxy($C_1$-$C_6$)alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, a liquid crystal mesogen, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from an alkyl, an alkoxy, amino, cycloalkyl, alkylalkoxy, a fluoroalkyl, a cyanoalkyl, a cyanoalkoxy and mixtures thereof.

Further, although not limiting herein, when P is a polymerizable group, the polymerizable group can be any functional group adapted to participate in a polymerization reaction. Non-limiting examples of polymerization reactions include those described in the definition of "polymerization" in *Hawley's Condensed Chemical Dictionary Thirteenth Edition*, 1997, John Wiley & Sons, pages 901-902, which disclosure is incorporated herein by reference. For example, although not limiting herein, polymerization reactions include: "addition polymerization," in which free radicals are the initiating agents that react with the double bond of a monomer by adding to it on one side at the same time producing a new free electron on the other side; "condensation polymerization," in which two reacting molecules combine to form a larger molecule with elimination of a small molecule, such as a water molecule; and "oxidative coupling polymerization." Further, non-limiting examples of polymerizable groups include hydroxy, acryloxy, methacryloxy, 2-(acryloxy)ethylcarbamyl, 2-(methacryloxy)ethylcarbamyl, isocyanate, aziridine, allylcarbonate, and epoxy, e.g., oxiranylmethyl.

Moreover, P can be chosen from a main-chain or a side-chain liquid crystal polymer and a liquid crystal mesogen. As used herein, the term liquid crystal "mesogen" means rigid rod-like or disc-like liquid crystal molecules. Further, as used herein the term "main-chain liquid crystal polymer" refers to a polymer having liquid crystal mesogens within the backbone (i.e., the main chain) structure of the polymer. As used herein the term "side-chain liquid crystal polymer" refers to a polymer having liquid crystal mesogens attached to the polymer at the side chains. Although not limiting herein, generally, the mesogens are made up of two or more aromatic rings that restrict the movement of a liquid crystal polymer. Examples of suitable rod-like liquid crystal mesogens include without limitation: substituted or unsubstituted aromatic esters, substituted or unsubstituted linear aromatic compounds, and substituted or unsubstituted terphenyls. According to another specific, non-limiting embodiment, P can be chosen from a steroid, for example and without limitation, a cholesterolic compound.

Non-limiting examples of thermally reversible photochromic pyrans from which the photochromic group PC can be chosen include benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline) naphthopyrans, spiro(indoline)benzopyrans, spiro(indoline) naphthopyrans, spiro(indoline)quinopyrans and spiro(indoline)pyrans. More specific examples of naphthopyrans and the complementary organic photochromic substances are described in U.S. Pat. No. 5,658,501, which are hereby specifically incorporated by reference herein. Spiro(indoline) pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines from which PC can be chosen include benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline) naphthoxazines, spiro(indoline)benzoxazines, spiro (indoline)fluoranthenoxazine, and spiro(indoline) quinoxazine. Non-limiting examples of photochromic fulgides from which PC can be chosen include: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

Further, wherein the photochromic-dichroic compound comprises at least two PCs, the PCs can be linked to one another via linking group substituents on the individual PCs.

For example, the PCs can be polymerizable photochromic groups or photochromic groups that are adapted to be compatible with a host material ("compatibilized photochromic group"). Non-limiting examples of polymerizable photochromic groups from which PC can be chosen and that are useful in conjunction with various non-limiting embodiments disclosed herein are disclosed in U.S. Pat. No. 6,113,814, which is hereby specifically incorporated by reference herein. Non-limiting examples of compatiblized photochromic groups from which PC can be chosen and that are useful in conjunction with various non-limiting embodiments disclosed herein are disclosed in U.S. Pat. No. 6,555,028, which is hereby specifically incorporated by reference herein.

Other suitable photochromic groups and complementary photochromic groups are described in U.S. Pat. Nos. 6,080,338 at column 2, line 21 to column 14, line 43; 6,136,968 at column 2, line 43 to column 20, line 67; 6,296,785 at column 2, line 47 to column 31, line 5; 6,348,604 at column 3, line 26 to column 17, line 15; 6,353,102 at column 1, line 62 to column 11, line 64; and 6,630,597 at column 2, line 16 to column 16, line 23; the disclosures of the aforementioned patents are incorporated herein by reference.

In addition to at least one lengthening agent (L), the photochromic compounds can further comprise at least one group represented by $R^1$ that is directly bonded to PC. Although not required, as previously discussed, the at least one lengthening agent (L) can be indirectly bonded to PC through the at least one group represented by $R^1$. That is, L can be a substituent on at least one group $R^1$ that is bonded to PC. According to various non-limiting embodiments disclosed herein, $R^1$ can be independently chosen for each occurrence from:

(i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;

(ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;

(iii) —CH(CN)$_2$ and —CH(COOX$_1$)$_2$, wherein X$_1$ is chosen from at least one of a lengthening agent L represented by Formula I above, H, $C_1$-$C_{12}$ alkyl that is unsubstituted or mono-substituted with phenyl, phenyl ($C_1$-$C_{12}$)alkyl that is mono-substituted with $C_1$-$C_{12}$ alkyl or $C_1$-$C_{12}$ alkoxy, and an aryl group that is unsubstituted, mono- or di-substituted, wherein each aryl substituent is independently chosen from $C_1$-$C_{12}$ alkyl and $C_1$-$C_{12}$ alkoxy;

(iv) —CH(X$_2$)(X$_3$), wherein:

(A) X$_2$ is chosen from at least one of a lengthening agent L represented by Formula I above, hydrogen, $C_1$-$C_{12}$alkyl and an aryl group that is unsubstituted, mono- or di-substituted, wherein each aryl substituent is independently chosen from $C_1$-$C_{12}$ alkyl and $C_1$-$C_{12}$ alkoxy; and (B) X$_3$ is chosen from at least one of —COOX$_1$, —COX$_1$, —COX$_4$, and —CH$_2$OX$_5$, wherein:

(1) X$_4$ is chosen from at least one of morpholino, piperidino, amino that is unsubstituted, mono- or di-substituted with $C_1$-$C_{12}$ alkyl, and an unsubstituted, mono or di-substituted group chosen from phenylamino and diphenylamino, wherein each substituent is independently chosen from $C_1$-$C_{12}$ alkyl or $C_1$-$C_{12}$ alkoxy; and (2) $X_5$ is chosen from a lengthening agent L represented by Formula I above, hydrogen, —C(O)$X_2$, $C_1$-$C_{12}$ alkyl that is unsubstituted or mono-substituted with ($C_1$-$C_{12}$)alkoxy or phenyl, phenyl($C_1$-$C_{12}$)alkyl that is mono-substituted with ($C_1$-$C_{12}$) alkoxy, and an aryl group that is unsubstituted, mono- or di-substituted, wherein each aryl substituent is independently chosen from $C_1$-$C_{12}$ alkyl and $C_1$-$C_{12}$ alkoxy;

(v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:

(A) a lengthening agent L represented by Formula I above;

(B) —C(O)$X_6$, wherein $X_6$ is chosen from at least one of: a lengthening agent L represented by Formula I above, H, $C_1$-$C_{12}$ alkoxy, phenoxy that is unsubstituted, mono- or di-substituted with $C_1$-$C_{12}$ alkyl or $C_1$-$C_{12}$ alkoxy, an aryl group that is unsubstituted, mono- or di-substituted with $C_1$-$C_{12}$ alkyl or $C_1$-$C_{12}$ alkoxy, an amino group that is unsubstituted, mono- or di-substituted with $C_1$-$C_{12}$ alkyl, and a phenylamino group that is unsubstituted, mono- or di-substituted with $C_1$-$C_{12}$ alkyl or $C_1$-$C_{12}$ alkoxy;

(C) aryl, haloaryl, $C_3$-$C_7$ cycloalkylaryl, and an aryl group that is mono- or di-substituted with $C_1$-$C_{12}$ alkyl or $C_1$-$C_{12}$alkoxy;

(D) $C_1$-$C_{12}$ alkyl, $C_3$-$C_7$ cycloalkyl, $C_3$-$C_7$ cycloalkyloxy($C_1$-$C_{12}$)alkyl, aryl($C_1$-$C_{12}$)alkyl, aryloxy($C_1$-$C_{12}$)alkyl, mono- or di-($C_1$-$C_{12}$)alkylaryl($C_1$-$C_{12}$)alkyl, mono- or di-($C_1$-$C_{12}$)alkoxyaryl($C_1$-$C_{12}$)alkyl, haloalkyl, and mono($C_1$-$C_{12}$)alkoxy($C_1$-$C_{12}$)alkyl;

(E) $C_1$-$C_{12}$ alkoxy, $C_3$-$C_7$ cycloalkoxy; cycloalkyloxy ($C_1$-$C_{12}$)alkoxy, aryl($C_1$-$C_{12}$)alkoxy, aryloxy($C_1$-$C_{12}$)alkoxy, mono- or di-($C_1$-$C_{12}$)alkylaryl($C_1$-$C_{12}$) alkoxy, and mono- or di-($C_1$-$C_{12}$)alkoxyaryl($C_1$-$C_{12}$) alkoxy;

(F) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(G) —O$X_7$ and —N($X_7$)$_2$, wherein $X_7$ is chosen from:
(1) a lengthening agent L represented by Formula I above, hydrogen, $C_1$-$C_{12}$ alkyl, $C_1$-$C_{12}$ acyl, phenyl ($C_1$-$C_{12}$)alkyl, mono($C_1$-$C_{12}$)alkyl substituted phenyl($C_1$-$C_{12}$)alkyl, mono($C_1$-$C_{12}$)alkoxy substituted phenyl($C_1$-$C_{12}$)alkyl; $C_1$-$C_{12}$ alkoxy($C_1$-$C_{12}$) alkyl; $C_3$-$C_7$ cycloalkyl; mono($C_1$-$C_{12}$)alkyl substituted $C_3$-$C_7$ cycloalkyl, $C_1$-$C_{12}$ haloalkyl, allyl, benzoyl, mono-substituted benzoyl, naphthoyl or mono-substituted naphthoyl, wherein each of said benzoyl and naphthoyl substituents are independently chosen from $C_1$-$C_{12}$ alkyl, and $C_1$-$C_{12}$ alkoxy;

(2) —CH($X_8$)$X_9$, wherein $X_8$ is chosen from a lengthening agent L represented by Formula I above, H or $C_1$-$C_{12}$ alkyl; and $X_9$ is chosen from a lengthening agent L represented by Formula I above, —CN, —CF$_3$, or —COO$X_{10}$, wherein $X_{10}$ is chosen from a lengthening agent L represented by Formula I above, H or $C_1$-$C_{12}$ alkyl;

(3) —C(O)$X_6$; and (4) tri($C_1$-$C_{12}$)alkylsilyl, tri($C_1$-$C_{12}$)alkoxysilyl, di($C_1$-$C_{12}$)alkyl($C_1$-$C_{12}$alkoxy)silyl, or di($C_1$-$C_{12}$) alkoxy($C_1$-$C_{12}$ alkyl)silyl;

(H) —S$X_{11}$, wherein $X_{11}$ is chosen from a lengthening agent L represented by Formula I above, $C_1$-$C_{12}$ alkyl, an aryl group that is unsubstituted, or mono- or di-substituted with $C_1$-$C_{12}$ alkyl, $C_1$-$C_{12}$ alkoxy or halogen;

(I) a nitrogen containing ring represented by Formula i:

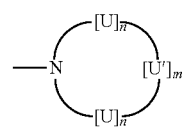

wherein:
(1) n is an integer chosen from 0, 1, 2, and 3, provided that if n is 0, U' is U, and each U is independently chosen for each occurrence from —CH$_2$—, —CH ($X_{12}$)—, —C($X_{12}$)$_2$—, —CH($X_{13}$)—, —C($X_{13}$)$_2$—, and —C($X_{12}$)($X_{13}$)—, wherein $X_{12}$ is chosen from a lengthening agent L represented by Formula I above and $C_1$-$C_{12}$ alkyl, and $X_{13}$ is chosen from a lengthening agent L represented by Formula I above, phenyl and naphthyl, and (2) U' is chosen from U, —O—, —S—, —S(O)—, —NH—, —N($X_{12}$)— or —N($X_{13}$)—, and m is an integer chosen from 1, 2, and 3; and (J) a group represented by one of Formula ii or iii:

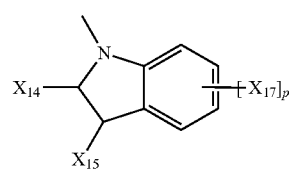

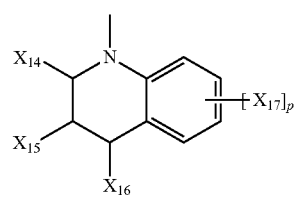

wherein $X_{14}$, $X_{15}$, and $X_{16}$ are independently chosen for each occurrence from a lengthening agent L represented by Formula I above, $C_1$-$C_{12}$ alkyl, phenyl and naphthyl, or $X_{14}$ and $X_{15}$ together form a ring of 5 to 8 carbon atoms; p is an integer chosen from 0, 1, or 2, and $X_{17}$ is independently chosen for each occurrence from a lengthening agent L represented by Formula I above, $C_1$-$C_{12}$ alkyl, $C_1$-$C_{12}$ alkoxy and halogen;

(vi) an unsubstituted or mono-substituted group chosen from pyrazolyl, imidazolyl, pyrazolinyl, imidazolinyl, pyrrolidinyl, phenothiazinyl, phenoxazinyl, phenazinyl and acridinyl, wherein each substituent is independently chosen from a lengthening agent L represented by Formula I above, $C_1$-$C_{12}$ alkyl, $C_1$-$C_{12}$ alkoxy, phenyl, hydroxy, amino and halogen;

(vii) a group represented by one of Formula iv or v:

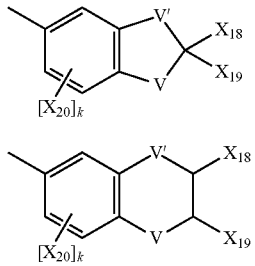

wherein (A) V' is independently chosen in each formula from —O—, —CH—, $C_1$-$C_6$ alkylene, and $C_3$-$C_7$ cycloalkylene, (B) V is independently chosen in each formula from —O— or —N($X_{21}$)—, wherein $X_{21}$ is from a lengthening agent L represented by Formula I above, hydrogen, $C_1$-$C_{12}$ alkyl, and $C_2$-$C_{12}$ acyl, provided that if V is —N($X_{21}$)—, V' is —$CH_2$—, (C) $X_{18}$ and $X_{19}$ are each independently chosen from a lengthening agent L represented by Formula I above, hydrogen and $C_1$-$C_{12}$ alkyl, and (D) k is chosen from 0, 1, and 2, and each $X_{20}$ is independently chosen for each occurrence from a lengthening agent L represented by Formula I above, $C_1$-$C_{12}$ alkyl, $C_1$-$C_{12}$ alkoxy, hydroxy and halogen;

(viii) a group represented by Formula vi:

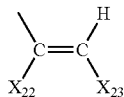

wherein (A) $X_{22}$ is chosen from a lengthening agent L represented by Formula I above, hydrogen and $C_1$-$C_{12}$ alkyl, and (B) $X_{23}$ is chosen from a lengthening agent L represented by Formula I above or an unsubstituted, mono-, or di-substituted group chosen from naphthyl, phenyl, furanyl and thienyl, wherein each substituent is independently chosen for each occurrence from $C_1$-$C_{12}$ alkyl, $C_1$-$C_{12}$ alkoxy, and halogen;

(ix) —C(O)$X_{24}$, wherein $X_{24}$ is chosen from a lengthening agent L represented by Formula I above, hydroxy, $C_1$-$C_{12}$ alkyl, $C_1$-$C_{12}$ alkoxy, phenyl that is unsubstituted or mono-substituted with $C_1$-$C_{12}$ alkyl or $C_1$-$C_{12}$ alkoxy, amino that is unsubstituted, mono- or di-substituted with at least one of $C_1$-$C_{12}$ alkyl, phenyl, benzyl, and napthyl;

(x) —$OX_7$ and —N($X_7$)$_2$, wherein $X_7$ is as set forth above;

(xi) —$SX_{11}$, wherein $X_{11}$ is as set forth above;

(xii) the nitrogen containing ring represented by Formula iv, which is set forth above;

(xiii) the group represented by one of Formula v or vi, which are set forth above; and (xiv) immediately adjacent $R^1$ groups together a group represented by one of Formula vii, viii, and ix:

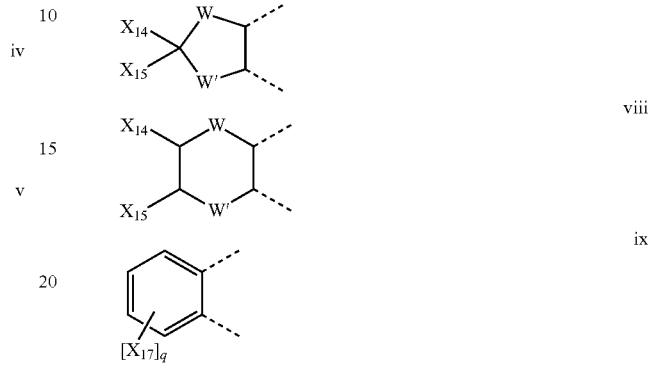

wherein (A) W and W' are independently chosen for each occurrence from —O—, —N($X_7$)—, —C($X_{14}$)—, —C($X_{17}$)—, (wherein $X_7$, $X_{14}$, and $X_{17}$ are as set forth above), (B) $X_{14}$, $X_{15}$ and $X_{17}$ are as set forth above, and (C) q is an integer chosen from 0, 1, 2, 3, and 4.

According to one non-limiting embodiment, the photochromic-dichroic compound can be a photochromic pyran that is represented by Formula II:

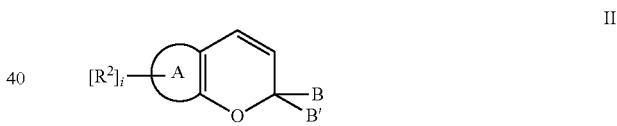

wherein A is an aromatic ring or a fused aromatic ring chosen from: naphtho, benzo, phenanthro, fluorantheno, antheno, quinolino, thieno, furo, indolo, indolino, indeno, benzofuro, benzothieno, thiopheno, indeno-fused naphtho, heterocyclic-fused naphtho, and heterocyclic-fused benzo; and B and B' each can be independently chosen from:

(i) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;

(ii) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ polyoxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;

(iii) —CH(CN)$_2$ and —CH(COO$X_1$)$_2$, wherein $X_1$ is as set forth above;

(iv) —CH(X₂)(X₃), wherein X₂ and X₃ are as set forth above;
(v) an unsubstituted, mono-, di-, or tri-substituted aryl group, such as phenyl, naphthyl, phenanthryl, or pyrenyl; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein the substituents are independently chosen for each occurrence from:
   (A) a lengthening agent L represented by Formula I above;
   (B) —C(O)X₆, wherein X₆ is as set forth above;
   (C) aryl, haloaryl, C₃-C₇ cycloalkylaryl, and an aryl group that is mono- or di-substituted with C₁-C₁₂ alkyl or C₁-C₁₂ alkoxy;
   (D) C₁-C₁₂ alkyl, C₃-C₇ cycloalkyl, C₃-C₇ cycloalkyloxy(C₁-C₁₂)alkyl, aryl(C₁-C₁₂)alkyl, aryloxy(C₁-C₁₂)alkyl, mono- or di-(C₁-C₁₂)alkylaryl(C₁-C₁₂)alkyl, mono- or di-(C₁-C₁₂)alkoxyaryl(C₁-C₁₂)alkyl, haloalkyl, and mono(C₁-C₁₂)alkoxy(C₁-C₁₂)alkyl;
   (E) C₁-C₁₂ alkoxy, C₃-C₇ cycloalkoxy; cycloalkyloxy (C₁-C₁₂)alkoxy; aryl(C₁-C₁₂)alkoxy, aryloxy(C₁-C₁₂)alkoxy, mono- or di-(C₁-C₁₂)alkylaryl(C₁-C₁₂)alkoxy, and mono- or di-(C₁-C₁₂)alkoxyaryl(C₁-C₁₂)alkoxy;
   (F) amido, amino, mono- or di-alkylamino, diarylamino, piperazino, N—(C₁-C₁₂)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;
   (G) —OX₇ and —N(X₇)₂, wherein X₇ is as set forth above;
   (H) —SX₁₁, wherein X₁₁ is as set forth above;
   (I) the nitrogen containing ring represented by Formula i, which is set forth above; and
   (J) the group represented by one of Formula ii or iii, which are set forth above;
(vi) an unsubstituted or mono-substituted group chosen from pyrazolyl, imidazolyl, pyrazolinyl, imidazolinyl, pyrrodlinyl, phenothiazinyl, phenoxazinyl, phenazinyl, and acridinyl, wherein each substituent is independently chosen from a lengthening agent L, C₁-C₁₂ alkyl, C₁-C₁₂ alkoxy, phenyl, hydroxy, amino or halogen;
(vii) the group represented by one of Formula iv or v, which are set forth above; and
(viii) the group represented by Formula vi, which is set forth above.

Alternatively, B and B' together can form: (a) an unsubstituted, mono- or di-substituted fluoren-9-ylidene, wherein each of said fluoren-9-ylidene substituents are chosen from C₁-C₄ alkyl, C₁-C₄ alkoxy, fluoro and chloro; (b) a saturated C₃-C₁₂ spiro-monocyclic hydrocarbon ring, e.g., cyclopropylidene, cyclobutylidene, cyclopentylidene, cyclohexylidene, cycloheptylidene, cyclooctylidene, cyclononylidene, cyclodecylidene cycloundecylidene, cyclododecylidene; (c) a saturated C₇-C₁₂ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1] octylidene, bicyclo[3.3.1]nonan-9-ylidene, bicyclo[4.3.2] undecane; or (d) a saturated C₇-C₁₂-spiro-tricyclic hydrocarbon rings, e.g., tricyclo[2.2.1.0²,⁶]heptylidene, tricyclo [3.3.1.1³,⁷]decylidene, i.e., adamantylidene, and tricyclo [5.3.1.1²,⁶]dodecylidene. Further according to various non-limiting embodiments discussed in more detail below, B and B' together can form indolino or benzoindolino that is unsubstituted or substituted with at least one group represented by R².

Referring again to Formula II, according to various non-limiting embodiments, "i" can be an integer chosen from 0 to the total available positions on A, and each R² can be independently chosen for each occurrence from: (i) a lengthening agent L represented by Formula □ (above) and (ii) a group represented by R¹ (above); provided that the photochromic-dichroic compound represented by Formula II comprises at least one lengthening agent (L) represented by Formula I above.

Thus, for example, in Formula II, "i" can be at least 1 and at least one of the R² groups can be a lengthening agent L. Additionally or alternatively, the photochromic-dichroic compound can comprise at least one R² group, at least one B group, or at least one B' group that is substituted with a lengthening agent L. Thus, for example and without limitation, L can be directly bonded to the pyran group, for example, wherein i is at least 1 and R² is L, or it can be indirectly bonded to the pyran group, for example, as a substituent on an R², B, or B' group such that L extends the pyran group in an activated state such that the absorption ratio of the photochromic compound is enhanced as compared to the unextended pyran group. For example, although not limiting herein, the B or B' group can be a phenyl group that is mono-substituted with a lengthening agent L.

For example, according to various non-limiting embodiments, the photochromic-dichroic compound can be a naphtho[1,2-b]pyran represented by Formula III:

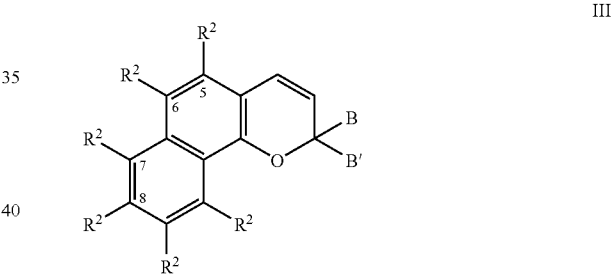

III wherein: (a) at least one of: the R² substituent in the 6-position, the R² substituent in the 8-position, B and B' comprises a lengthening agent L; (b) the R² substituent in the 6-position together with the R² substituent in the 5-position forms a group represented by one of Formula x to Formula xiv:

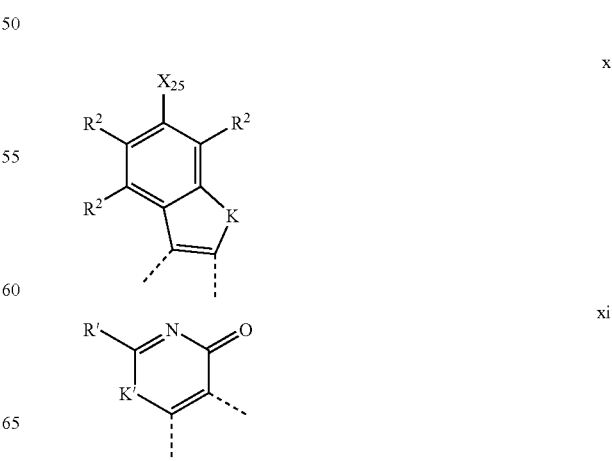

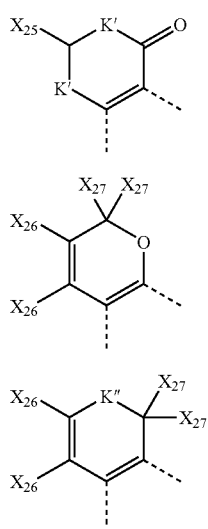

wherein K is chosen from —O—, —S—, —N(X₇)—; and an unsubstituted C or a C substituted with alkyl, hydroxy, alkoxy, oxo, or aryl; K' is —C—, —O—, or —N(X₇)—; K" is chosen from —O— or —N(X₇)—; $X_{25}$ is a group represented by $R^2$ (which is set forth above in detail); $X_{26}$ can be chosen from hydrogen, alkyl, aryl, or together form benzo or naphtho; and each $X_{27}$ is chosen from alkyl and aryl or together are oxo; provided that at least one of: the $R^2$ substituent in the 8-position, $X_{25}$, K, K', K", B or B' comprises a lengthening agent L; or (c) the $R^2$ substituent in the 6-position together with the $R^2$ substituent in the 7-position from an aromatic group chosen from benzeno and naphtho, provided that at least one of: the $R^2$ substituent in the 8-position, B and B' comprises a lengthening agent L.

Further, according to other non-limiting embodiments, the photochromic-dichroic compound can be an indeno-fused naphtho[1,2-b]pyran represented by Formula IV:

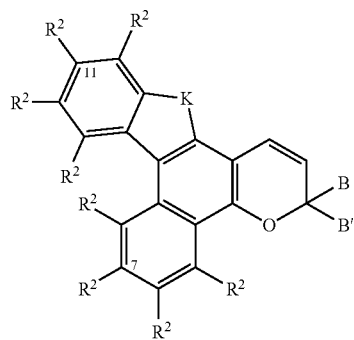

wherein K is as set forth above, and at least one of: the $R^2$ substituent in the 11-position, the $R^2$ substituent in the 7-position, K, B and B' comprises a lengthening agent L. Further, according to one specific non-limiting embodiment, at least of: the $R^2$ substituent in the 11-position and the $R^2$ substituent in the 7-position is a lengthening agent L.

According to other non-limiting embodiments, the photochromic-dichroic compound can be a naphtho[2,1-b]pyran represented by Formula V:

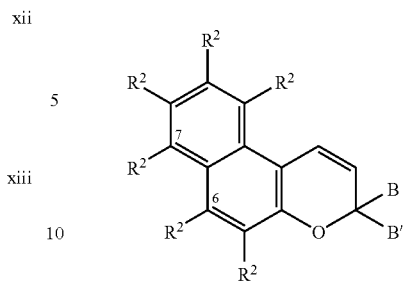

wherein at least one of: the $R^2$ substituent in the 6-position, the $R^2$ substituent in the 7-position, B, and B' comprises a lengthening agent L. More specifically, according to one non-limiting embodiment, at least one of: the $R^2$ substituent in the 6-position and the $R^2$ substituent in the 7-position is a lengthening agent L.

Further, according to still other non-limiting embodiments, the photochromic-dichroic compound can be a benzopyran comprising a structure represented by Formula VI:

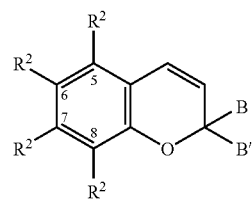

wherein: (a) at least one of: the $R^2$ substituent in the 5-position, the $R^2$ substituent in the 7-position, B or B' comprises a lengthening agent L; or (b) at least one of: the R substituent in the 5-position and the $R^2$ substituent in the 7-position, together with an immediately adjacent $R^2$ substituent, (i.e., the $R^2$ substituent in the 7-position together with an $R^2$ substituent in the 6- or 8-positions, or the $R^2$ substituent in the 5-position together with an R substituent in the 6-position) forms a group represented by Formula x to xiv (set forth above), provided that only one of the $R^2$ substituent in the 5-position and the $R^2$ substituent in the 7-position join together with the $R^2$ substituent in the 6-position, and provided that at least one of: the $R^2$ substituent in the 5-position, the $R^2$ substituent in the 7-position, $X_{25}$, K, K', K", B or B' comprises a lengthening agent L.

Non-limiting examples of specific photochromic-dichroic compounds suitable for use in the oriented polymeric sheet of the present invention included those disclosed in United States Published Patent Application 2005/0012998 A1 at paragraphs [0089]-[0151] the specified portions of which are incorporated by reference herein.

A general reaction sequence for forming photochromic-dichroic materials that can be used in the various embodiments of the present invention is disclosed in United States Published Patent Application 2005/0012998 A1 at paragraphs [0252]-[0339] the specified portions of which are incorporated by reference herein.

Obviously, if desired the polymeric sheet of the present invention can comprise a plurality of photochromic-dichroic compounds. Although not limiting herein, when two or more photochromic-dichroic compounds are used in combination, the photochromic-dichroic compounds can be chosen to complement one another to produce a desired color or hue.

For example, mixtures of photochromic-dichroic compounds can be used according to certain non-limiting embodiments disclosed herein to attain certain activated colors, such as a near neutral gray or near neutral brown. See, for example, U.S. Pat. No. 5,645,767, column 12, line 66 to column 13, line 19, the disclosure of which is specifically incorporated by reference herein, which describes the parameters that define neutral gray and brown colors. Additionally or alternatively, the at polymeric sheet can comprise mixtures of photochromic-dichroic compounds having complementary linear polarization states. For example, the photochromic-dichroic compounds can be chosen to have complementary linear polarization states over a desired range of wavelengths to produce a polymeric sheet that is capable of polarizing light over the desired range of wavelengths. Still further, mixtures of complementary photochromic-dichroic compounds having essentially the same polarization states at the same wavelengths can be chosen to reinforce or enhance the overall linear polarization achieved. For example, according to one non-limiting embodiment, the oriented polymeric sheet having the first state and the second state can comprise at least two at least partially aligned photochromic-dichroic compounds, wherein the at least two at least partially aligned photochromic-dichroic compounds have at least one of: complementary colors and complementary linear polarization states.

Additionally, the polymeric composition used to prepare the polymeric sheet of the present invention can comprise any of a wide variety of additives to influence or enhance one or more of the processing and/or performance properties of the polymeric sheet. Non-limiting examples of such additives can include dyes, dichroic dyes, photochromic dyes, alignment promoters, kinetic enhancing additives, photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, and adhesion promoters (such as hexanediol diacrylate and/or coupling agents).

Non-limiting examples of suitable dyes that can be used include organic dyes that are capable of imparting a desired color or other optical property to the at least partial coating.

As used herein, the term "alignment promoter" means an additive that can facilitate at least one of the rate and uniformity of the alignment of a material to which it is added.

Non-limiting examples of kinetic enhancing additives that can be present in the polymeric sheet according to the present invention can include epoxy-containing compounds, organic polyols, and/or plasticizers. More specific examples of such kinetic enhancing additives are disclosed in U.S. Pat. No. 6,433,043 and U.S. Patent Publication No. 2003/0045612, which are hereby specifically incorporated by reference herein.

Non-limiting examples of photoinitiators that can comprise the polymeric sheet according to the present invention can include cleavage-type photoinitiators and abstraction-type photoinitiators. Non-limiting examples of cleavage-type photoinitiators include acetophenones, α-aminoalkylphenones, benzoin ethers, benzoyl oximes, acylphosphine oxides and bisacylphosphine oxides or mixtures of such initiators. A commercial example of such a photoinitiator is DARO-CURE® 4265, which is available from Ciba Chemicals, Inc. Non-limiting examples of abstraction-type photoinitiators include benzophenone, Michler's ketone, thioxanthone, anthraquinone, camphorquinone, fluorone, ketocoumarin or mixtures of such initiators.

Another non-limiting example of a photoinitiator that can comprise the polymeric sheet in accordance with the present invention is a visible light photoinitiator. Non-limiting examples of suitable visible light photoinitiators are set forth at column 12, line 11 to column 13, line 21 of U.S. Pat. No. 6,602,603, which is specifically incorporated by reference herein.

Non-limiting examples of thermal initiators can include organic peroxy compounds and azobis(organonitrile) compounds. Specific non-limiting examples of organic peroxy compounds that are useful as thermal initiators include peroxymonocarbonate esters, such as tertiarybutylperoxy isopropyl carbonate; peroxydicarbonate esters, such as di(2-ethylhexyl)peroxydicarbonate, di(secondary butyl) peroxydicarbonate and diisopropylperoxydicarbonate; diacyperoxides, such as 2,4-dichlorobenzoyl peroxide, isobutyryl peroxide, decanoyl peroxide, lauroyl peroxide, propionyl peroxide, acetyl peroxide, benzoyl peroxide and p-chlorobenzoyl peroxide; peroxyesters such as t-butylperoxy pivalate, t-butylperoxy octylate and t-butylperoxyisobutyrate; methylethylketone peroxide, and acetylcyclohexane sulfonyl peroxide. In one non-limiting embodiment the thermal initiators used are those that do not discolor the resulting polymerizate. Non-limiting examples of azobis(organonitrile) compounds that can be used as thermal initiators include azobis(isobutyronitrile), azobis(2,4-dimethylvaleronitrile) or a mixture thereof.

Non-limiting examples of polymerization inhibitors can include: nitrobenzene, 1,3,5,-trinitrobenzene, pbenzoquinone, chloranil, DPPH, $FeCl_3$, $CuCl_2$, oxygen, sulfur, aniline, phenol, p-dihydroxybenzene, 1,2,3-trihydroxybenzene, 2,4,6-trimethylphenol, as well as hydroquinones and derivatives thereof.

Also, the polymeric sheet of the present invention can further comprise at least one conventional dichroic compound. Non-limiting examples of suitable conventional dichroic compounds include azomethines, indigoids, thioindigoids, merocyanines, indans, quinophthalonic dyes, perylenes, phthaloperines, triphenodioxazines, indoloquinoxalines, imidazo-triazines, tetrazines, azo and (poly)azo dyes, benzoquinones, naphthoquinones, anthroquinone and (poly)anthroquinones, anthropyrimidinones, iodine and iodates. The dichroic material also can comprise a polymerizable dichroic compound. That is, the dichroic material can comprise at least one group that is capable of being polymerized (i.e., a "polymerizable group"). For example, although not limiting herein, in one non-limiting embodiment the at least one dichroic compound can have at least one alkoxy, polyalkoxy, alkyl, or polyalkyl substituent terminated with at least one polymerizable group.

Still further, the polymeric sheet of the present invention can comprise at least one conventional photochromic compound. As used herein, the term "conventional photochromic compound" includes both thermally reversible and non-thermally reversible (or photo-reversible) photochromic compounds. Generally, although not limiting herein, when two or more conventional photochromic materials are used in combination with each other or with a photochromic-dichroic compound, the various materials can be chosen to complement one another to produce a desired color or hue. For example, mixtures of photochromic compounds can be used according to certain non-limiting embodiments disclosed herein to attain certain activated colors, such as a near neutral gray or near neutral brown. See, for example, U.S. Pat. No.

5,645,767, column 12, line 66 to column 13, line 19, the disclosure of which is specifically incorporated by reference herein, which describes the parameters that define neutral gray and brown colors.

In some instances, the polymeric composition used to form the polymeric sheet of the present invention can comprise a solvent. Non-limiting examples of solvents that can be used to prepare the polymeric sheet according to various non-limiting embodiments disclosed herein include those that will dissolve solid components of the polymeric composition from which the polymeric sheet is prepared, that facilitate the forming the polymeric sheet, e.g., as by solvent casting or extrusion, those that are compatible with the sheet, the support layers and the elements and substrates, as described hereinbelow. Such solvents can include, but are not limited to, the following: propylene glycol monomethyl ether acetate and their derivates (sold as DOWANOL® industrial solvents), acetone, amyl propionate, anisole, benzene, butyl acetate, cyclohexane, dialkyl ethers of ethylene glycol, e.g., diethylene glycol dimethyl ether and their derivates (sold as CELLOSOLVE® industrial solvents), diethylene glycol dibenzoate, dimethyl sulfoxide, dimethyl formamide, dimethoxybenzene, ethyl acetate, isopropyl alcohol, methyl cyclohexanone, cyclopentanone, methyl ethyl ketone, methyl isobutyl ketone, methyl propionate, propylene carbonate, tetrahydrofuran, toluene, xylene, 2-methoxyethyl ether, 3-propylene glycol methyl ether, and mixtures thereof.

Generally, the polymeric composition comprising any of the previously mentioned polymers, photochromic-dichroic compounds, and additives can be blended together and then subjected to any of a variety of processing techniques known in the art to form the polymeric sheet of the present invention. Such techniques can include, for example, extrusion, solvent casting, calendering, blowing, molding, or combinations of such techniques. Alternatively, the polymeric composition comprising any of the previously mentioned polymers and additives can be blended together and subjected to any of a variety of processing techniques known in the art to form the polymeric sheet. Once the polymeric sheet is formed, a solution comprising the photochromic-dichroic material(s) can be incorporated into the sheet, such as by an imbibition process well know in the art, and the imbibed polymeric sheet then can be oriented to align the photochromic-dichroic material(s).

As previously mentioned, once formed, the polymeric sheet comprising the photochromic-dichroic material is oriented to align the photochromic-dichroic material by any of a variety of methods known in the art. For example, the polymeric sheet can be oriented by stretching, by calendering, by extruding, by blowing, by molding, or by a combination of any of the foregoing orientation techniques. It should be understood, depending upon the polymeric composition from which the sheet can be prepared, the polymeric sheet may be formed and oriented in one step such as, for example, by extrusion where the sheet is extruded and oriented simultaneously by the extrusion process itself. In a particular embodiment of the present invention, the polymeric sheet is oriented by stretching and/or extruding.

The oriented polymeric sheet thus formed then can be fixed in the oriented configuration by any of a variety of fixing means known in the art. For example, a polymeric sheet oriented by stretching can be fixed in the oriented configuration to prevent recovery of the sheet to the pre-stretched configuration by mechanically fixing means (such as by the use of clamps). Other means can include thermofixing or thermal annealing, i.e., fixing the oriented polymeric sheet by heating. Where the polymeric sheet is prepared from reactive (e.g., crosslinkable) polymeric components, the sheet can be formed, such as by extrusion or solvent casting, in such a way that the components do not react. Once formed, the polymeric sheet can be oriented then fixed in the oriented configuration by reacting (e.g., crosslinking, including self-crosslinking) the polymeric components. For example, such crosslinking can be effectuated by subjecting the oriented sheet to conditions which promote the reaction of the functional groups of any reactive polymeric components, e.g., subjecting the oriented sheet to heat or radiation including actinic (ultraviolet) and/or ionizing (electron beam) radiation. Also, when the oriented polymeric sheet is to be used in a multi-layer composite (as described below), lamination with at least a support layer may also serve to fix the polymeric sheet in the oriented configuration. In a further embodiment, the oriented polymeric sheet can be thermoformed and fixed in the oriented configuration upon cooling.

Depending upon the components used to prepare the oriented polymeric sheet, the method used to form the polymeric sheet, and its desired end use, the oriented polymeric sheet of the present invention can have a wide range of thicknesses. Generally, the oriented polymeric sheet has a thickness ranging from 2 to 3000 micrometers, such as from 10 to 1000 micrometers, or from 20 to 500 micrometers, or from 25 to 100 micrometers.

As previously mentioned, the present invention also is directed to a multilayer composite comprising at least a support layer; and an oriented polymeric sheet comprising a photochromic-dichroic material, such as any of the oriented polymeric sheets described above, wherein the sheet exhibits dichroism in an activated state. The oriented polymeric sheet has two opposing surfaces, and at least one surface of the sheet is connected to at least a portion of the support layer. The photochromic-dichroic material can include any of the aforementioned photochromic-dichroic materials. In an embodiment of the present invention, the photochromic-dichroic material is adapted to transition from a first state to a second state in response to at least actinic radiation, and to linearly polarize at least transmitted radiation in at least the second state.

As used herein the term "connected to" means in direct contact with an object or indirect contact with an object through one or more other structures or materials, at least one of which is in direct contact with the object. Thus, according to various non-limiting embodiments disclosed herein, the oriented polymeric sheet can be in direct contact with at least a portion of the support layer (i.e., substrate) or it can be in indirect contact with at least a portion of the support layer (or substrate) through one or more other structures or materials. For example, although not limiting herein, the oriented polymeric sheet can be in contact with one or more coatings, other polymeric sheets, or combinations thereof, at least one of which is in direct contact with at least a portion of the support layer (or substrate).

Generally speaking, the support layers (i.e., substrates) of the multilayer composites in accordance with various non-limiting embodiments disclosed herein can include, but are not limited to, substrates formed from organic materials, inorganic materials, or combinations thereof (for example, composite materials). Non-limiting examples of substrates that can be used in accordance with various non-limiting embodiments disclosed herein are described in more detail below.

Specific, non-limiting examples of organic materials that may be used to form the support layer or substrates disclosed herein include polymeric materials, for examples, homopolymers and copolymers, prepared from the monomers and mixtures of monomers disclosed in U.S. Pat. No. 5,962,617 and in U.S. Pat. No. 5,658,501 from column 15, line 28 to column 16, line 17, the disclosures of which U.S. patents are specifically incorporated herein by reference. For example, such polymeric materials can be thermoplastic or thermoset polymeric materials, can be transparent or optically clear, and can have any refractive index required. Non-limiting examples of such disclosed monomers and polymers include: polyol(allyl carbonate) monomers, e.g., allyl diglycol carbonates such as diethylene glycol bis(allyl carbonate), which monomer is sold under the trademark CR-39 by PPG Industries, Inc.; polyurea-polyurethane (polyurea-urethane) polymers, which are prepared, for example, by the reaction of a polyurethane prepolymer and a diamine curing agent, a composition for one such polymer being sold under the trademark TRIVEX by PPG Industries, Inc.; polyol(meth)acryloyl terminated carbonate monomer; diethylene glycol dimethacrylate monomers; ethoxylated phenol methacrylate monomers; diisopropenyl benzene monomers; ethoxylated trimethylol propane triacrylate monomers; ethylene glycol bismethacrylate monomers; poly(ethylene glycol) bismethacrylate monomers; urethane acrylate monomers; poly(ethoxylated bisphenol A dimethacrylate); poly(vinyl acetate); poly(vinyl alcohol); poly(vinyl chloride); poly(vinylidene chloride); polyethylene; polypropylene; polyurethanes; polythiourethanes; thermoplastic polycarbonates, such as the carbonate-linked resin derived from bisphenol A and phosgene, one such material being sold under the trademark LEXAN; polyesters, such as the material sold under the trademark MYLAR; poly (ethylene terephthalate); polyvinyl butyral; poly(methyl methacrylate), such as the material sold under the trademark PLEXIGLAS, polyolefinic materials such as poly(cyclic) olefins and copolymers thereof, for example the materials sold under the tradename ARTON available from USR Corporation, and ZEONORFILM available from Zeon Chemicals L.P.; polyamides; and polymers prepared by reacting polyfunctional isocyanates with polythiols or polyepisulfide monomers, either homopolymerized or co- and/or terpolymerized with polythiols, polyisocyanates, polyisothiocyanates and optionally ethylenically unsaturated monomers or halogenated aromatic-containing vinyl monomers. Also contemplated are copolymers of such monomers and blends of the described polymers and copolymers with other polymers, for example, to form block copolymers or interpenetrating network products.

While not limiting herein, according to various non-limiting embodiments disclosed herein, the substrate can be an ophthalmic substrate. As used herein the term "ophthalmic substrate" means lenses, partially formed lenses, and lens blanks. Non-limiting examples of organic materials suitable for use in forming ophthalmic substrates according to various non-limiting embodiments disclosed herein include, but are not limited to, the art-recognized polymers that are useful as ophthalmic substrates, e.g., organic optical resins that are used to prepare optically clear castings for optical applications, such as ophthalmic lenses.

Other non-limiting examples of organic materials suitable for use in forming the substrates according to various non-limiting embodiments disclosed herein include both synthetic and natural organic materials, including without limitation: opaque or translucent polymeric materials, for example, the microporous polyolefinic synthetic printing sheet sold under the tradename TESLIN by PPG Industries, Inc., natural and synthetic textiles, and cellulosic materials such as, paper and wood.

Non-limiting examples of inorganic materials suitable for use in forming the substrates according to various non-limiting embodiments disclosed herein include glasses, minerals, ceramics, and metals. For example, in one non-limiting embodiment the substrate can comprise glass. In other non-limiting embodiments, the substrate can have a reflective surface, for example, a polished ceramic substrate, metal substrate, or mineral substrate. In other non-limiting embodiments, a reflective coating or layer can be deposited or otherwise applied to a surface of an inorganic or an organic substrate to make it reflective or to enhance its reflectivity.

The support layer or substrate may be pretreated such as by chemically etching or plasma treating, or application of a caustic solution to enhance adhesion of the polymeric sheet thereto.

Further, according to certain non-limiting embodiments disclosed herein, the substrates may have a protective coating, such as, but not limited to, an abrasion-resistant coating, such as a "hard coat," on their exterior surfaces. For example, commercially available thermoplastic polycarbonate ophthalmic lens substrates are often sold with an abrasion-resistant coating already applied to its exterior surfaces because these surfaces tend to be readily scratched, abraded or scuffed. An example of such a lens substrate is the GENTEX™ polycarbonate lens (available from Gentex Optics). Therefore, as used herein the term "support layer" or "substrate" includes a support layer or substrate having one or more protective coatings, such as but not limited to an abrasion-resistant coating, on its surface(s).

Still further, the support layers or substrates according to various non-limiting embodiments disclosed herein can be untinted, tinted, linearly polarizing, circularly polarizing, elliptically polarizing, photochromic, or tinted-photochromic substrates. As used herein with reference to substrates the term "untinted" means substrates that are essentially free of coloring agent additions (such as, but not limited to, conventional dyes) and have an absorption spectrum for visible radiation that does not vary significantly in response to actinic radiation. Further, with reference to substrates the term "tinted" means substrates that have a coloring agent addition (such as, but not limited to, conventional dyes) and an absorption spectrum for visible radiation that does not vary significantly in response to actinic radiation.

In a non-limiting embodiment of the present invention, the oriented polymeric sheet is connected to at least a portion of a support layer or substrate comprising polycarbonate, poly (cyclic)alkenes, polyurethane, poly(urea)urethane, polythiourethane, polythio(urea)urethane, polyol(allyl carbonate), copolymers thereof, or mixtures thereof. In a further non-limiting embodiment, the support layer comprises cellulose acetate, cellulose diacetate, cellulose triacetate, cellulose acetate propionate, cellulose acetate butyrate, poly(vinyl acetate), poly(vinyl alcohol), poly(vinyl chloride), poly(vinylidene chloride), poly(ethylene terephthalate), polyester, polyurethane, poly(urea)urethane, polythiourethane, polythio(urea)urethane, polysulfone, polyolefin, polyamide, copolymers thereof, and/or mixtures thereof.

The multilayer composite can further comprise a protective layer connected to at least a portion of the polymeric sheet such that the polymeric sheet is interposed between the protective layer and the support layer (or substrate). The protective layer can comprise one or more polymeric sheets comprising any of the polymeric sheets described above. The protective layer also can comprise one or more sheets comprised of any of the previously mentioned materials suitable for use as the support layer or substrate(s). Further, the protective layer can comprise one or more coatings such as abrasion-resistant coatings, oxygen barrier-coatings, UV-shielding coatings, anti-reflective coatings, anti-fogging coatings, mirror coating, or combinations thereof. Moreover, the protective layer can comprise, in any combination, one or more sheets, for example a polymeric sheet, and one or more coatings applied to at least a portion of the sheet surface(s).

Further, for some applications, one or both of the support layer (or substrate) and the protective layer is non-birefringent. For purposes of the present invention, by "non-birefringent" is meant that one or both of the support and protective layers have very low (less than 0.006) to low birefringence (0.006 to 0.05).

In one non-limiting embodiment, the present invention is directed to an optical element comprising any of the previously described multilayer composites. As used herein the term "optical" means pertaining to or associated with light and/or vision. For example, according to various non-limiting embodiments disclosed herein, the optical element or device can be chosen from ophthalmic elements and devices, display elements and devices, windows, mirrors, and active and passive liquid crystal cell elements and devices.

As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intraocular lenses, magnifying lenses, and protective lenses or visors. As used herein the term "display" means the visible or machine-readable representation of information in words, numbers, symbols, designs or drawings. Non-limiting examples of display elements and devices include screens, monitors, and security elements. Non-limiting examples of security elements can include security marks and authentication marks that are connected to at least a portion of a substrate, such as and without limitation: access cards and passes, e.g., tickets, badges, identification or membership cards, debit cards etc.; negotiable instruments and non-negotiable instruments, e.g., drafts, checks, bonds, notes, certificates of deposit, stock certificates, etc.; government documents, e.g., currency, licenses, identification cards, benefit cards, visas, passports, official certificates, deeds etc.; consumer goods, e.g., software, compact discs ("CDs"), digital-video discs ("DVDs"), appliances, consumer electronics, sporting goods, cars, etc.; credit cards; and merchandise tags, labels and packaging.

For example, in one non-limiting embodiment, the display element can be a security element connected to at least a portion of a substrate. According to this non-limiting embodiment the security element comprises any of the previously described multi-layer composites. The security element can be a security mark and/or an authentication mark.

Further, the security element can be connected to at least a portion of a substrate chosen from an optically transparent substrate (support layer), an optically opaque substrate (support layer) and/or a reflective substrate (support layer). The substrate can comprise any of the materials described above in detail with respect to the support layer or substrate materials of the multi-layer composite of the present invention. According to certain non-limiting embodiments wherein a reflective substrate is required, if the substrate is not reflective or sufficiently reflective for the intended application, a reflective material can be first applied to at least a portion of the substrate before the security mark is applied thereto. For example, a reflective aluminum coating can be applied to the at least a portion of the substrate prior to forming the security element thereon. Still further, security element can be connected to at least a portion of a substrate (support layer) chosen from untinted substrates, tinted substrates, photochromic substrates, tinted-photochromic substrates, linearly polarizing substrates, circularly polarizing substrates, and/or elliptically polarizing substrates.

In one embodiment, the present invention is directed to a security element comprising an optically opaque material, such as a microporous, synthetic printing sheet (for example the microporous polyolefinic sheet comprising inorganic particulate filler material commercially available under the tradename TESLIN from PPG Industries, Inc.), and oriented polymeric sheet in accordance with the present invention in the form of linearly oriented fiber.

As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light.

As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. One non-limiting example of an active liquid crystal cell element or device is a liquid crystal display.

In the preparation of the multi-layer composites of the present invention, including the optical elements comprising the multi-layer composites as described immediately above, the oriented polymeric sheet comprising photochromic-dichroic material is connected to at least a portion of the support layer or substrate by any of a wide variety of techniques known in the art. For example, the oriented polymeric sheet can be connected to the support layer (substrate) by at least one of laminating, fusing, in-mold casting, and adhesively bonding the polymeric sheet to at least a portion of the support layer or substrate. As used herein, the in-mold casting can include a variety of casting techniques, such as but not limited to overmolding, wherein the sheet is placed in a mold and the substrate is formed (for example by casting) over at least a portion of the sheet; and injection molding, wherein the substrate is formed around the sheet. Further, the polymeric sheet can be laminated on a surface of a first portion of the substrate/support layer, such as an optical substrate, and the first portion of the substrate/support layer can be placed in a mold. Thereafter, a second portion of the substrate/support layer can be formed (for example, by casting) on top of the first portion of the substrate/support layer such that the polymeric layer is between the two portions of the substrate/support layer.

Various non-limiting embodiments disclosed herein are illustrated in the following non-limited examples.

EXAMPLES

Examples

Part A

In Part 1A of the following examples, the procedures used to make oriented photochromic films exhibiting dichroism according to various non-limiting embodiments disclosed herein are set forth in Examples 1A-11A and Comparative Example 1A. In Part 2A, the test procedures and results are described.

Part 1A: Photochromic-dichroic Film Preparation Procedures

Example 1A

Step 1-Extrusion

ARNITEL® EM550 TPE (5 g) which prior to use was dried in a vacuum oven at 100° C. for at least 8 hrs, and PHOTOSOL® 7-1502 photochromic dye (0.5 g) were added to a conical twin screw 5 cc mini-extruder from DSM Research, The Netherlands. The screw speed was gradually increased from 10 to 25 rpm during the 3 minutes of filling and was gradually increased from 50 to 100 rpm during the 10 minutes of mixing. The pressure during mixing was approximately 600 to 700 Newtons/cm$^2$ (N/cm$^2$). The temperature of the unit during filling was 225° C., during mixing was 230° C. and during collection of the polymer was 240° C. After mixing, the product of Step 1 was collected in an aluminum cup.

Step 2-Compression Molding

The product of Step 1 was placed between 2 sheets of polydimethylsiloxane and compression molded in a Dr. Collin compression molding 300G, Dr. Collin GmbH, Germany at a temperature of 220° C. and a pressure of 20 bar. The material was first molten at low pressure before pressure was applied.

Step 3-Film Stretching

From the product of Step 2, compression molded films strips were cut to a size of 3 cm by 1 cm. The samples were clamped at the ends and drawn over a hot-shoe, which was set at 100° C., to a draw ratio of 7, i.e., seven times the original length. The stretched sample was fixed between glass slides by applying paraffin oil to both sides of the stretched sample to ensure optical contact, applying a cyanoacrylate-based glue to the edges of each glass slide and connecting the glass slides together.

Example 2A

The procedure of Example 1A was followed except that PHOTOSOL® 7-1513 photochromic dye was used in place of PHOTOSOL® 7-1502 photochromic dye.

Example 3A

The procedure of Example 1A was followed except that PHOTOSOL® 7-1515 photochromic dye (0.25 g) was used in place of PHOTOSOL® 7-1502 photochromic dye (0.50 g).

Example 4A

The procedure of Example 1A was followed except that PHOTOSOL® 7-1570 photochromic dye (0.25 g) was used in place of PHOTOSOL® 7-1502 photochromic dye (0.50 g) and the temperature of the extruder was 240° C. instead of 235° C.

Example 5A

The procedure of Example 1A was followed except that PHOTOSOL® 7-1570 photochromic dye was used in place of PHOTOSOL® 7-1502 photochromic dye; ARNITEL® EM400 TPE was used in place of ARNITEL® EM550 TPE; and a hot press temperature of 230° C. was used in place of 220° C. Two samples identified as A and B were prepared. The A sample was drawn to a draw ratio of 7 and the B sample was drawn to a draw ratio of 6 and after stretching both films were allowed to relax to draw ratios of 5 and 4.5, respectively.

Example 6A

The procedure of Example 1A was followed except that PHOTOSOL® 7-1570 photochromic dye was used in place of PHOTOSOL® 7-1502 photochromic dye; an extruder temperature of 240° C. was used instead of 235° C. and a hot press temperature of 235° C. was used instead of 220° C. Two samples identified as A and B were prepared. The A sample was drawn to a draw ratio of 7 and the B sample was drawn to a draw ratio of 6 and after stretching, both films were allowed to relax to draw ratios of 6 and 5.5, respectively.

Example 7A

The procedure of Example 1A was followed except that PHOTOSOL® 7-1515 photochromic dye was used in place of PHOTOSOL® 7-1502 photochromic dye; ARNITEL® EM400 TPE was used in place of ARNITEL® EM550 TPE; and a hot press temperature of 230° C. was used in place of 220° C.; and the sample was stretched to a draw ratio of 6 instead of 7.

Example 8A

The procedure of Example 1A was followed except that PHOTOSOL® 7-1515 photochromic dye was used in place of PHOTOSOL® 7-1502 photochromic dye; and the sample was stretched to a draw ratio of 6 instead of 7.

Example 9A

The procedure of Example 1A was followed except that PHOTOSOL® 7-1515 photochromic dye was used in place of PHOTOSOL® 7-1502 photochromic dye; ARNITEL® EM630 TPE was used in place of ARNITEL® EM550 TPE; an extruder temperature of 240° C. was used instead of 235° C.; and the sample was stretched to a draw ratio of 6 instead of 7.

Example 10A

Step 1-Extrusion

PHOTOSOL® 7-1570 photochromic dye was mixed into a polymer matrix of ARNITEL® EM550 TPE at a concentration of 1% based on weight using counter rotating conical twin-screw extruder, model TW100, from HaakeBuchler Instruments Inc., Germany, at a temperature of 210° C. and throughput of 65 g/min to produce 3 Kg of product. The extruded polymer was wound on a bobbin using a winding unit from Barmag EKS6D, Germany.

Step 2-Granulating

The fiber from Step 1 was granulated into pellets using a pelletizing system from C.F. Scheer & Cie GmnbH & Co operated at room temperature for 4 hours to produce pellets having an average diameter of 1.5 mm and average length of 3.5 mm.

Step 3-Film Formation

The pellets from Step 2 were extruded using a single screw extruder, the Dr. Collin Teach-line E20T model that had a temperature profile of 200° C. at the beginning of the screw; 240° C. at the middle of the screw; 250° C. at the end of the screw and 260° C. at the exit of the extruder. The resulting extruded melt was formed into a film having a thickness of approximately 100 microns using chill-rollers model Tape Postex, from Haake TPI, Germany, operating at a speed faster than the extruder and which were cooled by the flow through of tap water at a temperature of about 20° C.

Step 4-Film Stretching

The product of Step 3 was passed over two sets of rollers in the Polymatic 4G model from Polymatic machinebouw, The Netherlands, where the second set of rollers was rotating at 7 times the speed of the first set of rollers. In between the rollers, a Polymatic hot-air oven set at 150° C. from Polymatic Machinebouw, The Netherlands, heated the film. After stretching, the film was wound on a bobbin using a winder unit from Barmag EKS6D, Germany. The resulting film had a thickness of 40 microns, an initial draw ratio of 7 and after relaxation a draw ratio of 5.5

Example 11A

The product of Example 10A was coated with a thin layer of a cyanoacrylate glue using a blade coater from R K Print Coat Instruments Ltd., United Kingdom. A cellulose triacetate film having a thickness of 80 microns from Island Polymer Industries GmbH, Germany, was placed on top of the adhesive coated film and pressure was applied using a weight of 5 Kilograms for 15 minutes. An initial inspection revealed that a reasonable degree of adhesion was obtained. The reasonable adhesion assessment was determined by the degree of difficulty in peeling off the cellulose triacetate film from multiple samples having different amounts of adhesive applied to the individual films.

Part 2A: Photochromic-dichroic Film Testing Procedures

The Absorption Ratio (AR) and the Fade Half Life for the samples prepared in Examples 1A-10A were both measured using a UV-VIS-NIR scanning spectrophotometer, model UV-3102 PC from Schimadzu, The Netherlands according to the following procedures. Samples of Examples 1A-4A and 7A-9A were tested at their fixed draw ratios and Examples 5-A, 6-A and 10-A were tested at their relaxed draw ratios.

Prior to measuring the Absorption Ratio, the samples were activated by exposure to UV-light from a Philips Original Home Solaria with an intensity of $+1.4 \cdot 10^{-3}$ W/cm$^2$ UV A for 10 minutes. A linear polarizer was placed in the measuring beam of the spectrophotometer. The absorption maximum at the peak wavelength for each PHOTOSOL® photochromic dye was recorded first with the draw direction of the polymer film parallel to the polarizer and then with the draw direction perpendicular to the polarizer. Prior to each measurement, the sample was activated for 10 minutes in front of the Home Solaria. A standard baseline correction was performed by subtracting the absorbance of the glass slide and oil from that of the sample. The Absorption Ratio was determined by dividing the larger absorption by the smaller absorption.

The Fade Half Life was determined by first activating the sample by exposure to UV-light from a Philips Original Home Solaria for 10 minutes and measuring the absorption as a function of the fading time at the peak wavelength for each PHOTOSOL® photochromic dye. A standard baseline correction was made by subtracting the absorbance of the unactivated film from that of the activated sample. The data was normalized by setting the highest absorbance to 1.0. The fade half life in seconds was determined by determining at what time the absorbance was 0.5. The results are listed in Table 1.

TABLE 1

| EXAMPLE NO. | Absorption Ratio | Fade half-life (seconds) |
|---|---|---|
| 1A | 3.4 | 125 |
| 2A | 5.3 | >600 |
| 3A | 6.1 | 201 |
| 4A | 8.0 | >600 |
| 5A-A | 2.8 | 93 |
| 5A-B | 2.6 | 96 |
| 6A-A | 4.7 | 417 |
| 6A-B | 3.1 | 376 |
| 7A | 6.3 | 65 |
| 8A | 6.1 | 201 |
| 9A | 3.2 | 252 |
| 10A | 9.6 | 77 |

Examples

Part B

In Part 1B of the following examples, the procedures used to make photochromic stretched films and their subsequent lamination or application on lenses according to various non-limiting embodiments disclosed herein are set forth in Examples 1B-9B. In Part 2B, the ABSORPTION RATIO TEST METHOD and results are described.

Part 1B: Photochromic-dichroic Film Preparation Procedures

Example 1B

Step 1-Strand Extrusion

PEBAX® 5533 resin SA01 pellets were fed through the main hopper at a machine setting of 1.0 which was measured to deliver about 49.5 cubic centimeters (cm$^3$) per minute to a twin screw compounder, machine type NEF 970054 701/1 from APV Baker Ltd using a strand die. The screw speed of the compounder was 100 revolutions per minute (rpm), and the temperature profile from the main hopper to the die inclusive was: 170; 180; 190; 200; 210; 215; and 209° C. The exiting strand was cooled in a water bath having a temperature of approximately 14° C. Upon removal from the water bath, excess water was removed from the cooled strand using an air knife, model ELMO-G 2BH1300-1AA11 from Siemens. The cooled strand was then fed through a granulator model SGS50-E from C.F. Scheer & Cie GmmbH & Co. which was set at a machine setting of 2.5 to produce granulate that was similar in size to the original pellets. Since the granulate was of similar size and characteric of the original pellets, 5 grams of a combination of PHOTOSOL® 7-1570 photochromic dye (75 weight percent based on the total combination); IRGANOX® 3114 antioxidant (12.5 weight percent based on the total combination), and TINUVIN® 144 light stabilizer (12.5 weight percent based on the total combination). The combination was prepared by mixing the components in a glass beaker by hand using a spatula. The combination was added directly into the hopper all at once and the resulting PHOTOSOL® 7-1570 photochromic dye containing strand was collected in a suitable container. The resulting master batch showed a color gradient so further hand mixing in a transparent container was done to provide color consistency throughout the master batch.

Step 2-Thin Film Extrusion

The master batch from Step 1 was fed through a secondary side hopper operating at 5 rpm at a rate of 0.8 Kilogram/hour (Kg/hr) into a twin screw compounder, model MIC27/GL-36D from Leistritz having an extruder head with an attached Flexlip adjustment model MO 100/LAB from Verbruggen set at a screw speed of 100 rpm. The resulting film was fed through a Univex take-off system model number 843303007 from C.W. Brabender at a rate of 1.2 meter/minute (m/min) to produce a film with a thickness of approximately 80 microns and a width of approximately 11.7 cm.

Step 3-Film Stretching

Samples of the film from Step 2 were stretched on a Tensile Tester, model LR10K from Lloyd Instruments. Individual films were mounted on a purpose made self tightening, wide film clamp which was designed for use on the tensile tester. The initial film length of 40 millimeters (mm) was stretched a further 240 mm using a strain rate of 480 mm/min at an ambient temperature of about 19° C.

Step 4-Film Thermofixing

Following this stretching process, the films were clamped in a purpose made thin film clamp prepared from 2 aluminum frames that held the film in place and enabled the films to be removed from the tensile tester in a stretched state. The clamped film was subsequently placed in a thermostatically controlled air circulating oven from Carbolite at a temperature of 120° C. for a period of 10 minutes to thermofix the polymer in the stretched state.

Following the thermal cycle, the films were released from the clamp and allowed to cool at ambient temperature. Two films having different thickness were prepared. Film 1B-1 had a thickness of 52 microns and Film 1B-2 had a thickness of 86 microns. Film thickness was measured using a Mitutoyo digimatic indicator.

Example 2B

Laminated Film

A film prepared by the process of Example 1B having a thickness of approximately 90 microns was laminated as described in the following procedure. A sample of this film measuring 20 by 5 cm was coated with EverBuild's Mitre Fast Activator Spray by spraying the film for 4 seconds at a distance of 3 cm from the film and air-drying it for 30 seconds. The resulting film was laid out on a flat surface and held in position using weights. A film of TACPHAN® P 914 G4 triacetate cellulose measuring 7 by 25 cm and 180 microns thick from LOFO High Tech Film GmbH was coated with PRISM® 401 cyanoacrylate adhesive using a thin metal rod to spread the adhesive over the surface. The coated triacetate cellulose film was immediately pressed against the coated side of the film of Example 1B and allowed to cure for 30 seconds. The procedure was repeated for the opposite side of this film to produce a laminate of triacetate cellulose, the film (90 microns) of Example 1B and triacetate cellulose. Excess triacetate cellulose film was removed by cutting.

Example 3B

Film Coated Lens

A film prepared by the process of Example 1B having a thickness of 90 microns was manually coated with an "All plastics" Activator pen from Loctite, air dried for 30 seconds and placed in a purpose made, wide film clamp. A piano lens measuring 75 mm in diameter made of CR-607 monomer sold by PPG Industries Inc. was spin coated with 2 mL of PRISM® 401 cyanoacrylate adhesive on a spin coater model S-COAT 2001 from CPS Ltd using the following parameters: adhesive dispensing for 2.5 secs at 500 rpm followed by a fast spin for 6.5 secs at 1800 rpm. The coated side of the clamped film (90 microns) of Example 1B was manually pressed against the coated side of the lens and held in position for 30 seconds. The resulting laminated lens was cut free from the clamped film and any excess film was removed by cutting.

Example 4B

Film Coated Lens with a Hardcoat

The film coated lens of Example 3B was spin coated with 3.5 mL of DYMAX acrylate OP-4-20632 adhesive which as indicated by the supplier could be used as a hardcoat using a spin coater model S-COAT 2001 from CPS Ltd. The following spin coating parameters were used: dispensing for 2.5 secs at 500 rpm followed by a fast spin for 6.5 secs at 1850 RPM. The resulting coated lens was pre-cured with the DYMAX Blue Wave™ 200 Light Curing system for 56 seconds at a height of approximately 10 cm and post cured by UV exposure for approximately 40 seconds in an EYE® Ultraviolet system containing two V bulbs (gallium iodide). The system had been inerted with nitrogen to a level of less than 100 parts per million of oxygen.

Example 5B

Film of EXACT®0201 Plastomer

The procedure of Example 1B was followed except that in Step 1: EXACT®0201 plastomer reported to be an ethylene octene copolymer was used in place of PEBAX®5533; a custom made film die from CPS Ltd. of Galway, Ireland that enabled producing small scale film samples directly from the APV extruder was used; the temperature profile was the same except that the die temperature was 220° C.; and after the extruder was purged with virgin material to remove any residual impurities and a film of suitable visual quality was being extruded, a mixture of 10 g of a batch of EXACT®0201 plastomer containing 1 weight percent of IRGACURE® 651 antioxidant and 0.4 weight percent of IRGANOX® 1010 antioxidant and a 0.5 g addition of a combination of PHOTOSOL® 1570 and a 50/50 weight based stabilizer mixture of IRGANOX® 3114 and TINUVIN® 144 light stabilizer in a weight ratio of PHOTOSOL® 1570 to stabilizer of 1:1.7 was added directly onto the screw in the main hopper feed area. The extruded film from Step 1 was fed directly through the Univex take-off system at a rate of 1.0 m/min instead of 1.2 m/min.

Example 6B

Film of GRILAMID Ely 2702 NATUR Elastomer

The procedure of Example 5B was followed except that GRILAMID Ely 2702 NATUR elastomer was used in place of EXACT®0201 plastomer/IRGACURE® 651 antioxidant/ IRGANOX® 1010 antioxidant and 0.2 g of PHOTOSOL® 1570 was used in place of the 0.5 g quantity, and the stabilized photosol mixture was added to the side-hopper (that enables the addition of small samples) during the extrusion of virgin GRILAMID Ely 2702 NATUR elastomer at a machine setting of 1.0 which equates to 1.7 kilograms/hour (Kg/hr).

Example 7B

Film of PHOTOSOL® 7-1515 and Dichroic Dyes

The procedure of Example 1B was followed except that the granulator model SGS50-E from C.F. Scheer & Cie GmbH & Co. was set at 1.25 instead of 2.5; the PHOTOSOL® 1570 and stabilizers composition was replaced with PHOTOSOL® 7-1515 (6.034 g); proprietary dichroic dyes: yellow dichroic dye (0.112 g); red dichroic dye (0.229 g); and blue dichroic dye (0.66 g); and the final weight of the master batch was 250 g.

Example 8B

Laminated Film

The procedure of Example 7B was followed to produce a stretched film which was used in the procedure of Example 2B to produce a laminated film.

Example 9B

Film of PELLETHANE™ 80 AE Thermoplastic Polyurethane

The procedure of Example 5B was followed except that PELLETHANE™ 80 AE thermoplastic polyurethane was used in place of EXACT®0201 plastomer.

Part 2B: Photochromic-dichroic Film Testing Procedures
Absorption Ratio Test Method An optical bench was used in the ABSORPTION RATIO TEST METHOD to measure the average Absorption Ratios (AR) for each of the samples prepared in Examples 1B-9B as follows. Prior to testing, each of the samples was cut into sections that were at least 7 cm by 4 cm and held in a purpose made aluminum frame clamp. The clamped samples were exposed to activating radiation for 5 minutes at a distance of 15 centimeters (cm) from a bank of four UV Tubes BLE-7900B supplied by Spectronics Corp and then placed for 30 minutes at a distance of 15 cm from a bank of four UVless tubes F40GO supplied by General Electric and finally held in the dark for at least 30 minutes. Afterwards the clamped sample was placed in a spring loaded holder on the optical bench. The optical bench included an activating light source (an Oriel Model 66011 300-Watt Xenon arc lamp fitted with a Melles Griot 04 IES 211 high-speed computer controlled shutter that momentarily closed during data collection so that stray light would not interfere with the data collection process, a Schott 3 mm KG-2 band-pass filter, which removed short wavelength radiation, neutral density filter(s) for intensity attenuation and a condensing lens for beam collimation) positioned at a 300 angle of incidence to the surface of the sample.

An HL-2000 tungsten halogen lamp from Ocean Optics equipped with a fiber optic cable used for monitoring response measurements was positioned in a perpendicular manner to the surface of the sample. Linear polarization of the light source was achieved by passing the light from the end of the cable through a Moxtek, Proflux Polarizer held in a computer driven, motorized rotation stage (Model M-061-PD from Polytech, PI). The monitoring beam was set so that the one polarization plane (0°) was perpendicular to the plane of the optical bench table and the second polarization plane (90°) was parallel to the plane of the optical bench table. The samples were run in air, at room temperature (73° F.±5° F.) maintained by the lab air conditioning system.

To conduct the measurements, the samples were exposed to 1.17 W/m$^2$ of UVA from the activating light source for 5 to 15 minutes to activate the photochromic-dichroic compound. An International Light Research Radiometer (Model IL-1700) with a detector system (Model SED033 detector, B Filter, and diffuser) was used to verify exposure prior to each test. Light from the monitoring source that was polarized in the 0° polarization plane was then passed through sample and focused on a 2" integrating sphere, which was connected to a Ocean Optics 2000 spectrophotometer using a single function fiber optic cable. The spectral information after passing through the sample was collected using Ocean Optics OOI-Base32 and OOIColor software, and PPG propriety software. While the photochromic-dichroic compound was activated, the position of the polarizing sheet was rotated back and forth to polarize the light from the monitoring light source to the 90° polarization plane and back. Data was collected at 3-second intervals during activation. For each test, rotation of the polarizers was adjusted to collect data in the following sequence of polarization planes: 0°, 90°, 90°, 0° etc.

Response measurements, in terms of a change in optical density between the unactivated or bleached state and the activated or colored state were determined by establishing the initial unactivated transmittance, opening the shutter from the Xenon lamp(s) and measuring the transmittance through activation at selected intervals of time. During the times of the actual transmission measurement, the Xenon beam was briefly closed to prevent light scattering.

Absorption spectra were obtained and analyzed for each sample using the Igor Pro software (available from WaveMetrics). The change in the absorbance for each sample was calculated by subtracting out the 0 time (i.e., unactivated) absorption measurement for each wavelength tested. Average absorbance values were obtained in the region of the activation profile where the photochromic response was saturated or nearly saturated (i.e., the regions where the absorbance did not increase or did not increase significantly over time) for each sample by averaging the absorbance taken at each time interval for each sample in this region (for each wavelength extracted were averaged of 5 to 100 data points). The average absorbance values in a predetermined range of wavelengths corresponding maximum-visible +/−5 nm were extracted for the 0° and 90° polarizations, and the absorption ratio for each wavelength in this range was calculated by dividing the larger average absorbance by the small average absorbance. For each wavelength extracted, 5 to 100 data points were averaged. The average absorption ratio for the sample was then calculated by averaging these individual absorption ratios. The lambda max or maximum lambda reported below is the wavelength where a peak in absorbance was observed for the sample in the crossed polarization state (sample polarization direction is 90 degrees to the Moxtek, Proflux Polarizer). The results are reported below wherein the First Fade Half Life ("T1/2") value is the time interval in seconds for the ΔOD of the activated form of the photochromic-dichroic material in the sample to reach one half the maximum ΔOD at 73.4° F. (23° C.), after removal of the activating light source. The Second Fade Half Life ("2T1/2") value is the time interval in seconds for the ΔOD of the activated form of the photochromic material in the sample to reach one quarter the maximum ΔOD at 73.4° F. (23° C.), after removal of the activating light cource. Samples that were not tested for the Second Fade Half Life are identified as NOT DETERMINED with the other results presented below in Table 2.

TABLE 2

| Example # | AR | Max λ nanometers | 1st T1/2 (seconds) | 2nd T1/2 (seconds) |
|---|---|---|---|---|
| 1B-1 | 6.97 | 556 | 124 | 312 |
| 1B-2 | 6.70 | 556 | 107 | 291 |
| 2B | 7.04 | 558 | 106 | 266 |
| 3B | 7.31 | 556 | 122 | NOT DETERMINED |
| 4B | 6.21 | 556 | 120 | NOT DETERMINED |
| 5B | 3.19 | 538 | 209 | NOT DETERMINED |
| 6B | 8.92 | 558 | 105 | 218 |
| 7B | 3.35 | 602 | 38 | 87 |
| 8B | 2.71 | 600 | 38 | NOT DETERMINED |
| 9B | 3.91 | 564 | 74 | 174 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Whereas the present invention has been described in connection with certain embodiments, the present invention is not limited to the particular embodiments disclosed, but is intended to cover modifications that are within the spirit and scope of the invention, as defined by the appended claims.

We claim:

1. An oriented polymeric sheet comprising a photochromic-dichroic material, wherein the sheet exhibits dichroism in an activated state,
wherein the photochromic-dichroic material transitions from a first state having a first absorbance spectrum to a second state having a second absorption spectrum different from the first absorption spectrum in response to at least actinic radiation, reverts back to the first state in response to thermal energy, and linearly polarizes at least transmitted radiation in at least the second state, the photochromic-dichroic material comprising a compound having
(a) at least one photochromic (PC) group chosen from a pyran, an oxazine, and a fulgide; and
(b) at least one lengthening agent L attached to the photochromic group and represented by:

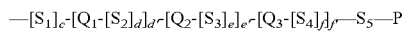

wherein:
(i) each $Q_1$, $Q_2$, and $Q_3$ is independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, thiol, amide, liquid crystal mesogens, halogen, $C_1$-$C_{18}$ alkoxy, poly($C_1$-$C_{18}$ alkoxy), amino, amino ($C_1$-$C_{18}$)alkylene, $C_1$-$C_{18}$alkylamino, di-($C_1$-$C_{18}$) alkylamino, $C_1$-$C_{18}$ alkyl, $C_2$-$C_{18}$ alkene, $C_2$-$C_{18}$ alkyne, $C_1$-$C_{18}$ alkyl($C_1$-$C_{18}$)alkoxy, $C_1$-$C_{18}$ alkoxycarbonyl, $C_1$-$C_{18}$ alkylcarbonyl, $C_1$-$C_{18}$ alkyl carbonate, aryl carbonate, $C_1$-$C_{18}$ acetyl, $C_3$-$C_{10}$ cycloalkyl, $C_3$-$C_{10}$ cycloalkoxy, isocyanato, amido, cyano, nitro, a straight-chain or branched $C_1$-$C_{18}$ alkyl group that is mono-substituted with cyano, halo, or $C_1$-$C_{18}$ alkoxy, or poly-substituted with halo, and a group represented by one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;
(ii) c, d, e, and f are each independently chosen from an integer ranging from 0 to 20, inclusive; and each $S_1$, $S_2$, $S_3$, $S_4$, and $S_5$ is independently chosen for each occurrence from a spacer unit chosen from:
(A) —(CH$_2$)$_g$—, —(CF$_2$)$_h$—, —Si(CH$_2$)$_g$—, —(Si[(CH$_3$)$_2$]O)$_h$—, wherein g is independently chosen for each occurrence from 1 to 20; h is a whole number from 1 to 16 inclusive;
(B) —N(Z)—, —C(Z)=C(Z)—, —C(Z)=N—, —C(Z')—C(Z')—, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and
(C) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;
provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other;
(iii) P is chosen from: aziridinyl, hydrogen, hydroxy, aryl, alkyl, alkoxy, amino, alkylamino, alkylalkoxy, alkoxyalkoxy, nitro, polyalkyl ether, ($C_1$-$C_6$)alkyl($C_1$-$C_6$)alkoxy($C_1$-$C_6$)alkyl, polyethyleneoxy, polypropyleneoxy, ethylene, acrylate, methacrylate, 2-chloroacrylate, 2-phenylacrylate, cryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from alkyl, alkoxy, amino, cycloalkyl, alkylalkoxy, fluoroalkyl, cyanoalkyl, cyanoalkoxy and mixtures thereof; and
(iv) d', e' and f' are each independently chosen from 0, 1, 2, 3, and 4, provided that a sum of d'+e'+f' is at least 3, wherein said oriented polymeric sheet comprises an elastomeric polymer.

2. The polymeric sheet of claim 1, having an absorption ratio of at least 1.5 in the activated state.

3. The polymeric sheet of claim 2, having an absorption ratio ranging from 3 to 20 in the activated state.

4. The polymeric sheet of claim 1 wherein the sheet is oriented by extruding, by stretching, by calendering, by blowing and/or by molding.

5. The polymeric sheet of claim 4, wherein the sheet is oriented by stretching.

6. The polymeric sheet of claim 1, wherein the elastomeric polymer comprises a block copolymer comprising ether and/or ester linkages in the copolymer backbone.

7. The polymeric sheet of claim 6, wherein the elastomeric block copolymer comprises poly(amide-ether) block copolymers, poly(ester-ether) block copolymers, poly(ether-urethane) block copolymers, poly(ester-urethane) block copolymers and/or poly(ether-urea) block copolymers.

8. The polymeric sheet of claim 1, wherein the photochromic-dichroic material comprises a compound comprising:
(a) the at least one photochromic (PC) group chosen from a pyran, an oxazine, and a non-thermally reversible fulgide; and
(b) the at least one lengthening agent L attached to the at least one photochromic group and represented by:

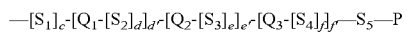

wherein:
(i) each $Q_1$, $Q_2$, and $Q_3$ is independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, thiol, amide, liquid crystal mesogens, halogen, $C_1$-$C_{18}$alkoxy, poly($C_1$-$C_{18}$ alkoxy), amino, amino($C_1$-$C_{18}$)alkylene, $C_1$-$C_{18}$alkylamino, di-($C_1$-$C_{18}$)alkylamino, $C_1$-$C_{18}$ alkyl, $C_2$-$C_{18}$alkene, $C_2$-$C_{18}$ alkyne, $C_1$-$C_{18}$ alkyl($C_1$-$C_{18}$)alkoxy, $C_1$-$C_{18}$ alkoxycarbonyl, $C_1$-$C_{18}$ alkylcarbonyl, $C_1$-$C_{18}$ alkyl carbonate, aryl carbonate, $C_1$-$C_{18}$ acetyl, $C_3$-$C_{10}$ cycloalkyl, $C_3$-$C_{10}$ cycloalkoxy, isocyanate, amido, cyano, nitro, a straight-chain or branched $C_1$-$C_{18}$ alkyl group that is mono-substituted with cyano, halo, or $C_1$-$C_{18}$ alkoxy, or poly-substituted with halo, and a group comprising one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;
(ii) c, d, e, and f are each independently chosen from an integer ranging from 0 to 20, inclusive; and each $S_1$, $S_2$, $S_3$, $S_4$, and $S_5$ is independently chosen for each occurrence from a spacer unit chosen from:
(A) —(CH$_2$)$_g$—, —(CF$_2$)$_h$—, —Si(CH$_2$)$_g$—, —(Si[(CH$_3$)$_2$]O)$_h$—, wherein g is independently chosen for each occurrence from 1 to 20; h is a whole number from 1 to 16 inclusive;
(B) —N(Z)—, —C(Z)=C(Z)—, —C(Z)=N—, —C(Z')—C(Z')—, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and
(C) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;
provided that when two spacer units comprising heteroatoms are linked together the spacer units are linked so that heteroatoms are not directly linked to each other and when $S_1$ and $S_5$ are linked to PC and P, respectively, they are linked so that two heteroatoms are not directly linked to each other;
(iii) P is chosen from: aziridinyl, hydrogen, hydroxy, aryl, alkyl, alkoxy, amino, alkylamino, alkylalkoxy, alkoxyalkoxy, nitro, polyalkyl ether, ($C_1$-$C_6$)alkyl ($C_1$-$C_6$)alkoxy($C_1$-$C_6$)alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from alkyl, alkoxy, amino, cycloalkyl, alkylalkoxy, fluoroalkyl, cyanoalkyl, cyanoalkoxy and mixtures thereof (iv) d', e' and f' are each independently chosen from 0, 1, 2, 3, and 4, provided that a sum of d'+e'+f' is at least 3.

9. The polymeric sheet of claim 8, wherein at least one of $Q_1$, $Q_2$, and $Q_3$ is a unsubstituted or a substituted heterocyclic group chosen from: isosorbitol, dibenzofuro, dibenzothieno, benzofuro, benzothieno, thieno, furo, dioxino, carbazolo, anthranilyl, azepinyl, benzoxazolyl, diazepinyl, dioazlyl, imidazolidinyl, imidazolyl, imidazolinyl, indazolyl, indoleninyl, indolinyl, indolizinyl, indolyl, indoxazinyl, isobenzazolyl, isoindolyl, isooxazolyl, isooxazyl, isopyrroyl, isoquinolyl, isothiazolyl, morpholino, morpholinyl, oxadiazolyl, oxathiazolyl, oxathiazyl, oxathiolyl, oxatriazolyl, oxazolyl, piperazinyl, piperazyl, piperidyl, purinyl, pyranopyrrolyl, pyrazinyl, pyrazolidinyl, pyrazolinyl, pyrazolyl, pyrazyl, pyridazinyl, pyridazyl, pyridyl, pyrimidinyl, pyrimidyl, pyridenyl, pyrrolidinyl, pyrrolinyl, pyrroyl, quinolizinyl, quinuclidinyl, quinolyl, thiazolyl, triazolyl, triazyl, N-arylpiperazino, aziridino, arylpiperidino, thiomorpholino, tetrahydroquinolino, tetrahydroisoquinolino, pyrryl, unsubstituted, mono- or di-substituted $C_4$-$C_{18}$ spirobicyclic amines, and unsubstituted, mono- or di-substituted $C_4$-$C_{18}$ spirotricyclic amines.

10. The polymeric sheet of claim 8, wherein at least one of $Q_1$, $Q_2$, and $Q_3$ is a unsubstituted or a substituted alicyclic group chosen from: cyclohexyl, cyclopropyl, norbornenyl, decalinyl, adamantanyl, bicyclooctane, per-hydrofluorene, and cubanyl.

11. The polymeric sheet of claim 8, wherein the compound further comprises at least one $R^1$ group attached to the at least one photochromic (PC) group, wherein each $R^1$ group is independently chosen for each occurrence from:

(a) hydrogen, $C_1$-$C_{12}$ alkyl, $C_2$-$C_{12}$ alkylidene, $C_2$-$C_{12}$ alkylidyne, vinyl, $C_3$-$C_7$ cycloalkyl, $C_1$-$C_{12}$ haloalkyl, allyl, halogen, and benzyl that is unsubstituted or mono-substituted with at least one of $C_1$-$C_{12}$ alkyl and $C_1$-$C_{12}$ alkoxy;

(b) phenyl that is mono-substituted at the para position with at least one substituent chosen from: $C_1$-$C_7$ alkoxy, linear or branched chain $C_1$-$C_{20}$ alkylene, linear or branched chain $C_1$-$C_4$ poly-oxyalkylene, cyclic $C_3$-$C_{20}$ alkylene, phenylene, naphthylene, $C_1$-$C_4$ alkyl substituted phenylene, mono- or poly-urethane($C_1$-$C_{20}$)alkylene, mono- or poly-ester($C_1$-$C_{20}$)alkylene, mono- or poly-carbonate($C_1$-$C_{20}$)alkylene, polysilanylene, polysiloxanylene and mixtures thereof, wherein the at least one substituent is connected to an aryl group of a photochromic material;

(c) —CH(CN)$_2$ and —CH(COOX$_1$)$_2$, wherein $X_1$ is chosen from at least one of a lengthening agent L represented by the formula above, hydrogen, $C_1$-$C_{12}$ alkyl that is unsubstituted or mono-substituted with phenyl, phenyl($C_1$-$C_{12}$)alkyl that is mono-substituted with $C_1$-$C_{12}$ alkyl or $C_1$-$C_{12}$ alkoxy, and an aryl group that is unsubstituted, mono- or di-substituted, wherein each aryl substituent is independently chosen from $C_1$-$C_{12}$ alkyl and $C_1$-$C_{12}$ alkoxy;

(d) —CH($X_2$)($X_3$), wherein:

(i) $X_2$ is chosen from at least one of a lengthening agent L represented by the formula above, hydrogen, $C_1$-$C_{12}$ alkyl, and an aryl group that is unsubstituted, mono- or di-substituted, wherein each aryl substituent is independently chosen from $C_1$-$C_{12}$ alkyl and $C_1$-$C_{12}$ alkoxy; and (ii) $X_3$ is chosen from at least one of —COOX$_1$, —COX$_1$, —COX$_4$, and —CH$_2$OX$_5$, wherein:

(A) $X_4$ is chosen from at least one of morpholino, piperidino, amino that is unsubstituted, mono- or di-substituted with $C_1$-$C_{12}$ alkyl, and an unsubstituted, mono or di-substituted group chosen from phenylamino and diphenylamino, wherein each substituent is independently chosen from $C_1$-$C_{12}$ alkyl or $C_1$-$C_{12}$ alkoxy; and (B) $X_5$ is chosen from a lengthening agent L represented by the formula above, hydrogen, —C(O)$X_2$, $C_1$-$C_{12}$ alkyl that is unsubstituted or mono-substituted with ($C_1$-$C_{12}$)alkoxy or phenyl, phenyl($C_1$-$C_{12}$)alkyl that is mono-substituted with ($C_1$-$C_{12}$)alkoxy, and an aryl group that is unsubstituted, mono- or di-substituted, wherein each aryl substituent is independently chosen from $C_1$-$C_{12}$ alkyl and $C_1$-$C_{12}$ alkoxy;

(e) an unsubstituted, mono-, di-, or tri-substituted aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl; wherein each substituent is independently chosen for each occurrence from:

(i) a lengthening agent L represented by the formula above;

(ii) —C(O)$X_6$, wherein $X_6$ is chosen from at least one of: a lengthening agent L represented by the formula above, hydrogen, $C_1$-$C_{12}$ alkoxy, phenoxy that is unsubstituted, mono- or di-substituted with $C_1$-$C_{12}$ alkyl or $C_1$-$C_{12}$ alkoxy, an aryl group that is unsubstituted, mono- or di-substituted with $C_1$-$C_{12}$ alkyl or $C_1$-$C_{12}$ alkoxy, an amino group that is unsubstituted, mono- or di-substituted with $C_1$-$C_{12}$ alkyl, and a phenylamino group that is unsubstituted, mono- or di-substituted with $C_1$-$C_{12}$ alkyl or $C_1$-$C_{12}$ alkoxy;

(iii) aryl, haloaryl, $C_3$-$C_7$ cycloalkylaryl, and an aryl group that is mono- or di-substituted with $C_1$-$C_{12}$ alkyl or $C_1$-$C_{12}$ alkoxy;

(iv) $C_1$-$C_{12}$ alkyl, $C_3$-$C_7$ cycloalkyl, $C_3$-$C_7$ cycloalkyloxy ($C_1$-$C_{12}$)alkyl, aryl($C_1$-$C_{12}$)alkyl, aryloxy($C_1$-$C_{12}$) alkyl, mono- or di- ($C_1$-alkylaryl($C_1$-$C_{12}$)alkyl, mono- or di- ($C_1$-$C_{12}$)alkoxyaryl($C_1$-$C_{12}$)alkyl, haloalkyl, and mono($C_1$-$C_{12}$)alkoxy($C_1$-$C_{12}$)alkyl;

(v) $C_1$-$C_{12}$ alkoxy, $C_3$-$C_7$ cycloalkoxy; cycloalkyloxy($C_1$-$C_{12}$)alkoxy; aryl($C_1$-$C_{12}$)alkoxy, aryloxy($C_1$-$C_{12}$) alkoxy, mono- or di- ($C_1C_{12}$)alkylaryl($C_1$-$C_{12}$)alkoxy, and mono- or di- ($C_1$-$C_{12}$)alkoxyaryl ($C_1$-$C_{12}$)alkoxy;

(vi) amido, amino, mono- or di-alkylamino, diarylamino, piperazino, N—($C_1$-$C_{12}$)alkylpiperazino, N-arylpiperazino, aziridino, indolino, piperidino, morpholino, thiomorpholino, tetrahydroquinolino, tetrahydroisoquinolino, pyrrolidyl, hydroxy, acryloxy, methacryloxy, and halogen;

(vii) —OX$_7$ or —N($X_7$)$_2$, wherein $X_7$ is chosen from:

(A) a lengthening agent L represented by the formula above, hydrogen, $C_1$-$C_{12}$ alkyl, $C_1$-$C_{12}$ acyl, phenyl ($C_1$-$C_{12}$)alkyl, mono($C_1$-$C_{12}$)alkyl substituted phenyl ($C_1$-$C_{12}$) alkyl, mono($C_1$-$C_{12}$)alkoxy substituted phenyl($C_1$-$C_{12}$)alkyl; $C_1$-$C_{12}$ alkoxy($C_1$-$C_{12}$)alkyl; $C_3$-$C_7$ cycloalkyl; mono($C_1$-$C_{12}$)alkyl substituted $C_3$-$C_7$ cycloalkyl, $C_1$-$C_{12}$ haloalkyl, allyl, benzoyl, mono-subsituted benzoyl, naphthoyl or mono-substituted naphthoyl, wherein each of said benzoyl and naphthoyl substituents are independently chosen from $C_1$-$C_{12}$ alkyl, and $C_1$-$C_{12}$ alkoxy;

(B) —CH($X_8$)$X_9$, wherein $X_8$ is chosen from a lengthening agent L represented by the formula above, hydrogen or $C_1$-$C_{12}$ alkyl; and $X_9$ is chosen from a lengthening agent L represented by the formula above, —CN, —CF$_3$, or —COOX$_{10}$, wherein $X_{10}$ is chosen from a lengthening agent L represented by the formula above, hydrogen or $C_1$-$C_{12}$ alkyl;

(C) —C(O)$X_6$; or (D) tri($C_1$-$C_{12}$)alkylsilyl, tri($C_1$-$C_{12}$)alkoxysilyl, di($C_1$-$C_{12}$)alkyl($C_1$-$C_{12}$alkoxy)silyl, or di($C_1$-$C_{12}$)alkoxy ($C_1$-$C_{12}$alkyl)silyl;

(viii) S$X_{11}$, wherein $X_{11}$ is chosen from a lengthening agent L represented by the formula above, $C_1$-$C_{12}$ alkyl, an aryl group that is unsubstituted, or mono- or di-substituted with $C_1$-$C_{12}$ alkyl, $C_1$-$C_{12}$ alkoxy, or halogen;

(ix) a nitrogen containing ring represented by Formula i;

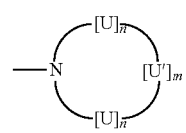

i wherein (A) n is an integer chosen from 0, 1, 2, and 3, provided that if n is 0, U' is U, and each U is independently chosen for each occurrence from —CH$_2$—, —CH ($X_{12}$)—, —C($X_{12}$)$_2$—, —CH($X_{13}$)—, —C($X_{13}$)$_2$—, and —C($X_{12}$)($X_{13}$)—, wherein $X_{12}$ is chosen from a lengthening agent L represented by the formula above and $C_1$-$C_{12}$ alkyl, and $X_{13}$ is chosen from a lengthening agent L represented by the formula above, phenyl and naphthyl, and (B) U' is chosen from U, —O—, —S—, —S(O)—, —NH—, —N($X_{12}$)— or —N($X_{13}$)—, and m is an integer chosen from 1, 2, and 3, and (x) a group represented by Formula ii or iii:

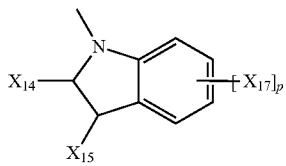

ii

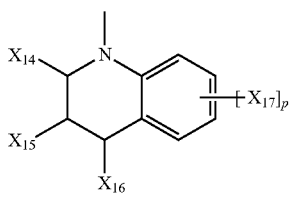

iii wherein $X_{14}$, $X_{15}$, and $X_{16}$ are independently chosen for each occurrence from a lengthening agent L represented by the formula above, $C_1$-$C_{12}$ alkyl, phenyl or naphthyl, or $X_{14}$ and $X_{15}$ together form a ring of 5 to 8 carbon atoms; p is an integer chosen from 0, 1, or 2, and $X_{17}$ is independently chosen for each occurrence from a lengthening agent L represented by the formula above, $C_1$-$C_{12}$ alkyl $C_1$-$C_{12}$ alkoxy, or halogen;

(f) an unsubstituted or mono-substituted group chosen from pyrazolyl, imidazolyl, pyrazolinyl, imidazolinyl, pyrrolidinyl, phenothiazinyl, phenoxazinyl, phenazinyl, or acridinyl, wherein each substituent is independently chosen from a lengthening agent L represented by the formula above, $C_1$-$C_{12}$ alkyl, $C_1$-$C_{12}$ alkoxy, phenyl, hydroxy, amino or halogen;

(g) a group represented by Formula iv or v:

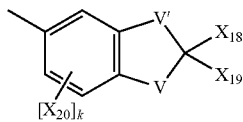

iv

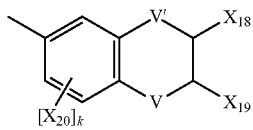

v wherein
(i) V' is independently chosen in each formula from —O—, —CH—, $C_1$-$C_6$ alkylene, and $C_3$-$C_7$ cycloalkylene,
(ii) V is independently chosen in each formula from —O— or —N($X_{21}$)—, wherein $X_{21}$ is from a lengthening agent L represented by the formula above, hydrogen, $C_1$-$C_{12}$ alkyl, and $C_2$-$C_{12}$ acyl, provided that if V is —N($X_{21}$)—, V' is —$CH_2$—,
(iii) $X_{18}$ and $X_{19}$ are each independently chosen from a lengthening agent L represented by the formula above, hydrogen and $C_1$-$C_{12}$ alkyl, and
(iv) k is chosen from 0, 1, and 2, and each $X_{20}$ is independently chosen for each occurrence from a lengthening agent L represented by the formula above, $C_1$-$C_{12}$ alkyl, $C_1$-$C_{12}$ alkoxy, hydroxy and halogen;

(h) a group represented by Formula vi:

vi (i) $X_{22}$ is chosen from a lengthening agent L represented by the formula above, hydrogen and $C_1$-$C_{12}$ alkyl, and
(ii) $X_{23}$ is chosen from a lengthening agent L represented by the formula above and an unsubstituted, mono-, or di-substituted group chosen from naphthyl, phenyl, furanyl and thienyl, wherein each substituent is independently chosen for each occurrence from $C_1$-$C_{12}$ alkyl, $C_1$-$C_{12}$ alkoxy, and halogen;

(i) —C(O)$X_{24}$, wherein $X_{24}$ is chosen from a lengthening agent L represented by the formula above, hydroxy, $C_1$-$C_{12}$ alkyl, $C_1$-$C_{12}$ alkoxy, phenyl that is unsubstituted or mono-substituted with $C_1$-$C_{12}$ alkyl or $C_1$-$C_{12}$ alkoxy, amino that is unsubstituted, mono- or di-substituted with at least one of $C_1$-$C_{12}$ alkyl, phenyl, benzyl, and naphthyl;

(j) —$OX_7$ and —N($X_7$)$_2$;
(k) —$SX_{11}$;
(l) the nitrogen containing ring represented by Formula i;
(m) the group represented by one of Formula ii or iii; or
(n) immediately adjacent $R^1$ groups together form at a group represented by Formula vii, viii, or ix:

vii viii ix wherein
(i) W and W' are independently chosen for each occurrence from —O—, —N($X_7$)—, —C($X_{14}$)—, —C($X_{17}$)—,
(ii) $X_{14}$, $X_{15}$ and $X_{17}$ are as set forth above, and
(iii) q is an integer chosen from 0, 1, 2, 3, and 4.

12. The polymeric sheet of claim 1, further comprising an additive comprising dyes, dichroic dyes, photochromic dyes, alignment promoters, kinetic enhancing additives, photoinitiators, thermal initiators, polymerization inhibitors, solvents, light stabilizers, heat stabilizers, mold release agents, rheology control agents, leveling agents, free radical scavengers, and/or adhesion promoters.

13. The polymeric sheet according to claim 1, wherein the sheet is in the form of a fiber.

14. A multilayer composite comprising at least a support layer; and
an oriented polymeric sheet having two opposing surfaces and comprising a photochromic-dichroic material,
wherein the sheet exhibits dichroism in an activated state, and wherein at least one surface of the sheet is connected to at least a portion of the support layer,
wherein the photochromic-dichroic material transitions from a first state having a first absorption spectrum to a second state having a second absorption spectrum different from the first absorption spectrum in response to at least actinic radiation, reverts back to the first state in response to thermal energy, and linearly polarizes at least transmitted radiation in at least the second state,
the photochromic-dichroic material comprising a compound having
(a) at least one photochromic group chosen from a pyran, an oxazine, and a fulgide; and
(b) at least one lengthening agent L attached to the photochromic group and represented by:

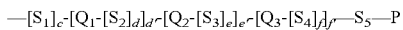

wherein:
(i) each $Q_1$, $Q_2$, and $Q_3$ is independently chosen for each occurrence from: a divalent group chosen from: an unsubstituted or a substituted aromatic group, an unsubstituted or a substituted alicyclic group, an unsubstituted or a substituted heterocyclic group, and mixtures thereof, wherein substituents are chosen from: a group represented by P, thiol, amide, liquid crystal mesogens, halogen, $C_1$-$C_{18}$ alkoxy, poly($C_1$-$C_{18}$ alkoxy), amino, amino($C_1$-$C_{18}$)alkylene, $C_1$-$C_{18}$ alkylamino, di-($C_1$-$C_{18}$)alkylamino, $C_1$-$C_{18}$ alkyl, $C_2$-$C_{18}$ alkene, $C_2$-$C_{18}$ alkyne, $C_1$-$C_{18}$ alkyl($C_1$-$C_{18}$) alkoxy, $C_1$-$C_{18}$ alkoxycarbonyl, $C_1$-$C_{18}$ alkylcarbonyl, $C_1$-$C_{18}$ alkyl carbonate, aryl carbonate, $C_1$-$C_{18}$ acetyl, $C_3$-$C_{10}$ cycloalkyl, $C_3$-$C_{10}$ cycloalkoxy, isocyanato, amido, cyano, nitro, a straight-chain or branched $C_1$-$C_{18}$ alkyl group that is mono-substituted with cyano, halo, or $C_1$-$C_{18}$ alkoxy, or poly-substituted with halo, and a group represented by one of the following formulae: -M(T)$_{(t-1)}$ and -M(OT)$_{(t-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and t is the valence of M;
(ii) c, d, e, and f are each independently chosen from an integer ranging from 0 to 20, inclusive; and each $S_1$, $S_2$, $S_3$, $S_4$, and $S_5$ is independently chosen for each occurrence from a spacer unit chosen from:
(A) —(CH$_2$)$_g$—, —(CF$_2$)$_h$—, —Si(CH$_2$)$_g$—, —(Si[(CH$_3$)$_2$]O)$_h$—, wherein g is independently chosen for each occurrence from 1 to 20; h is a whole number from 1 to 16 inclusive;
(B) —N(Z)—, —C(Z)=C(Z)—, —C(Z)=N—, —C(Z')—C(Z')—, wherein Z is independently chosen for each occurrence from hydrogen, $C_1$-$C_6$ alkyl, cycloalkyl and aryl, and Z' is independently chosen for each occurrence from $C_1$-$C_6$ alkyl, cycloalkyl and aryl; and
(C) —O—, —C(O)—, —C≡C—, —N=N—, —S—, —S(O)—, —S(O)(O)—, straight-chain or branched $C_1$-$C_{24}$ alkylene residue, said $C_1$-$C_{24}$ alkylene residue being unsubstituted, mono-substituted by cyano or halo, or poly-substituted by halo;
provided that when two spacer units comprising heteroatoms are linked together the spacer units are linked so that heteroatoms are not directly linked to each other and when S1 and S5 are linked to PC and P, respectively, they are linked so that two heteroatoms are not directly linked to each other;
(iii) P is chosen from: aziridinyl, hydrogen, hydroxy, aryl, alkyl, alkoxy, amino, alkylamino, alkylalkoxy, alkoxyalkoxy, nitro, polyalkyl ether, ($C_1$-$C_6$)alkyl($C_1$-$C_6$)alkoxy($C_1$-$C_6$)alkyl, polyethyleneoxy, polypropyleneoxy, ethylene, acrylate, methacrylate, 2-chloroacrylate, 2-phenylacrylate, acryloylphenylene, acrylamide, methacrylamide, 2-chloroacrylamide, 2-phenylacrylamide, epoxy, isocyanate, thiol, thioisocyanate, itaconic acid ester, vinyl ether, vinyl ester, a styrene derivative, siloxane, main-chain and side-chain liquid crystal polymers, ethyleneimine derivatives, maleic acid derivatives, fumaric acid derivatives, unsubstituted cinnamic acid derivatives, cinnamic acid derivatives that are substituted with at least one of methyl, methoxy, cyano and halogen, and substituted and unsubstituted chiral and non-chiral monovalent or divalent groups chosen from steroid radicals, terpenoid radicals, alkaloid radicals and mixtures thereof, wherein the substituents are independently chosen from alkyl, alkoxy, amino, cycloalkyl, alkylalkoxy, fluoroalkyl, cyanoalkyl, cyanoalkoxy and mixtures thereof; and
(iv) d', e' and f' are each independently chosen from 0, 1, 2, 3, and 4, provided that a sum of d' +e' +f' is at least 3,
wherein said oriented polymeric sheet comprises an elastomeric polymer.

15. The multilayer composite of claim 14, wherein the elastomeric polymer comprises a block copolymer comprising ether and/or ester linkages in the copolymer backbone.

16. The multilayer composite of claim 15, wherein the block copolymer comprises poly(amide-ether) block copolymers, poly(ester-ether) block copolymers, poly(ether-urethane) block copolymers, poly(ester-urethane) block copolymers, and/or poly(ether-urea) block copolymers.

17. The multilayer composite of claim 14, wherein the support layer comprises polycarbonate, polycyclic alkene, polyurethane, poly(urea)urethane, polythiourethane, polythio(urea)urethane, polyol(allyl carbonate), copolymers thereof, or mixtures thereof.

18. The multilayer composite of claim 14, wherein the support layer comprises a cellulose acetate, cellulose diacetate, cellulose triacetate, cellulose acetate propionate, cellulose acetate butyrate, poly(vinyl acetate), poly(vinyl alcohol), poly(vinyl chloride), poly(vinylidene chloride), poly(ethylene terephthalate), polyester, polyurethane, poly(urea)urethane, polythiourethane, polythio(urea)urethane, polysulfone, polyolefin, copolymers thereof, and/or mixtures thereof.

19. The multilayer composite of claim 14, further comprising a protective layer connected to at least a portion of the polymeric sheet such that the polymeric sheet is interposed between the protective layer and the support layer.

20. The multilayer composite of claim 19, wherein the protective layer comprises a protective coating comprising abrasion-resistant coatings, oxygen barrier-coatings, UV-shielding coatings, anti-reflective coatings, anti-fogging coatings, mirror coatings, or combinations thereof.

21. An optical element comprising the multilayer composite of claim 19.

22. The optical element of claim 21, wherein one or both of the support layer and the protective layer is non-birefringent.

23. An optical element comprising the multilayer composite of claim 14.

24. The optical element of claim 23, wherein the optical element comprises ophthalmic elements, display elements, windows, mirrors, and/or active and passive liquid crystal cell elements and devices.

25. The optical element of claim 24, wherein the ophthalmic element comprises corrective lenses, non-corrective lenses, contact lenses, intra-ocular lenses, magnifying lenses, protective lenses, or visors.

26. The optical element of claim 24, wherein the display element comprises screens, monitors and/or security elements.

27. The optical element of claim 26, wherein the security elements comprise an optically transparent material and/or an optically opaque material.

28. The optical element of claim 23, wherein the support layer comprises a substrate selected from untinted substrates, tinted substrates, photochromic substrates, tinted photochromic substrates, and linearly polarizing substrates.

29. The optical element of claim 23, wherein the support layer comprises polycarbonate, polyurethane, poly(urea)urethane, polythiourethane, polythio(urea)urethane, polycyclic alkenes, polyol(allyl carbonate), copolymers thereof, and/or mixtures thereof.

30. The optical element of claim 23, wherein the support layer comprises cellulose acetate, cellulose diacetate, cellulose triacetate, cellulose acetate propionate, cellulose acetate butyrate, poly(vinyl acetate), poly(vinyl alcohol), poly(vinyl chloride), poly(vinylidene chloride), poly(ethylene terephthalate), polyester, polyurethane, poly(urea)urethane, polythiourethane, polythio(urea)urethane, polysulfone, polyolefin, copolymers thereof, and/or mixtures thereof.

* * * * *